(12) United States Patent
Kim et al.

(10) Patent No.: US 11,529,122 B2
(45) Date of Patent: Dec. 20, 2022

(54) METHODS AND APPARATUSES FOR MEASURING TISSUE STIFFNESS CHANGES USING ULTRASOUND ELASTICITY IMAGING

(71) Applicants: University of Pittsburgh—Of the Commonwealth System of Higher Education, Pittsburgh, PA (US); The Regents of the University of Michigan, Ann Arbor, MI (US)

(72) Inventors: Kang Kim, Pittsburgh, PA (US); Jingping Xu, Shanghai (CN); Jonathan M Rubin, Ann Arbor, MI (US)

(73) Assignees: University of Pittsburgh—Of the Commonwealth System of Higher Education, Pittsburgh, PA (US); The Regents of the University of Michigan, Ann Arbor, MI (US)

(*) Notice: Subject to any disclaimer, the term of this patent is extended or adjusted under 35 U.S.C. 154(b) by 178 days.

(21) Appl. No.: 16/726,089

(22) Filed: Dec. 23, 2019

(65) Prior Publication Data

US 2020/0146654 A1    May 14, 2020

Related U.S. Application Data

(62) Division of application No. 15/389,036, filed on Dec. 22, 2016, now abandoned, which is a division of
(Continued)

(51) Int. Cl.
*A61B 8/08*    (2006.01)
*G01N 29/06*    (2006.01)
(Continued)

(52) U.S. Cl.
CPC ............... *A61B 8/485* (2013.01); *A61B 8/08* (2013.01); *A61B 8/085* (2013.01); *A61B 8/0858* (2013.01);
(Continued)

(58) Field of Classification Search
CPC ......... A61B 8/485; A61B 8/08; A61B 8/4281; A61B 8/4483; A61B 8/461; A61B 8/5223;
(Continued)

(56) References Cited

U.S. PATENT DOCUMENTS 5,474,070 A * 12/1995 Ophir .................. A61B 5/0048
600/437
5,524,636 A * 6/1996 Sarvazyan ........... A61B 1/0052
600/587

(Continued)

FOREIGN PATENT DOCUMENTS

KR    10-2011-0016527    2/2011

OTHER PUBLICATIONS

Glozman et al., "A Method for Characterization of Tissue Elastic Properties Combining Ultrasonic Computed Tomography with Elastography," *Journal of Ultrasound in Medicine*, vol. 29, pp. 387-389 (Mar. 2010).

(Continued)

*Primary Examiner* — Bo Joseph Peng
(74) *Attorney, Agent, or Firm* — Klarquist Sparkman, LLP

(57) ABSTRACT

A method of evaluating tissue stiffness of a target area includes positioning an ultrasound elasticity imaging apparatus adjacent a surface of an area of tissue where the target area is located and applying a dynamic range of force to the tissue. A plurality of ultrasound beams can be directed at the tissue and a plurality of ultrasound echoes can be acquired (Continued)

from the strained tissue in the target area to calculate an amount of developed strain within the target area.

8 Claims, 20 Drawing Sheets

Related U.S. Application Data application No. 14/119,050, filed as application No. PCT/US2012/039179 on May 23, 2012, now Pat. No. 9,554,777.

(60) Provisional application No. 61/489,169, filed on May 23, 2011.

(51) Int. Cl.
*G01N 29/07* (2006.01)
*A61B 8/00* (2006.01)

(52) U.S. Cl.
CPC .......... *A61B 8/4281* (2013.01); *A61B 8/4483* (2013.01); *A61B 8/461* (2013.01); *A61B 8/5223* (2013.01); *G01N 29/0654* (2013.01); *G01N 29/07* (2013.01); *G01N 2291/02475* (2013.01); *G01N 2291/0422* (2013.01)

(58) Field of Classification Search
CPC .. A61B 8/085; A61B 8/0858; G01N 29/0654; G01N 29/07; G01N 2291/02475; G01N 2291/0422

See application file for complete search history.

(56) References Cited

U.S. PATENT DOCUMENTS

| | | |
|---|---|---|
| 2007/0049824 A1 | 3/2007 | Konofagou et al. |
| 2007/0071295 A1* | 3/2007 | Jackson ................ G06T 7/0012 |
| | | 382/128 |
| 2008/0081994 A1 | 4/2008 | Kim et al. |
| 2010/0113937 A1 | 5/2010 | Matsumura et al. |
| 2011/0040187 A1 | 2/2011 | Matsumura |

OTHER PUBLICATIONS

Kim et al., "Noninvasive Ultrasound Elasticity Imaging (UEI) of Crohn's Disease: Animal Model," *Ultrasound in Medicine & Biology*, vol. 34, Issue 6, pp. 902-912 (Jun. 2008).

* cited by examiner

FIG. 2A
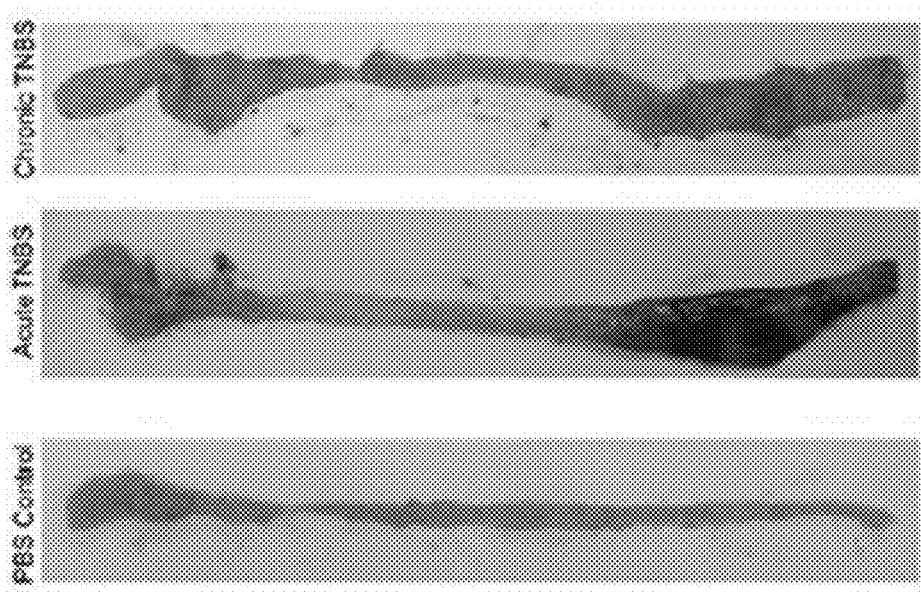
FIG. 2B H&E  Trichrome  alpha-SMA
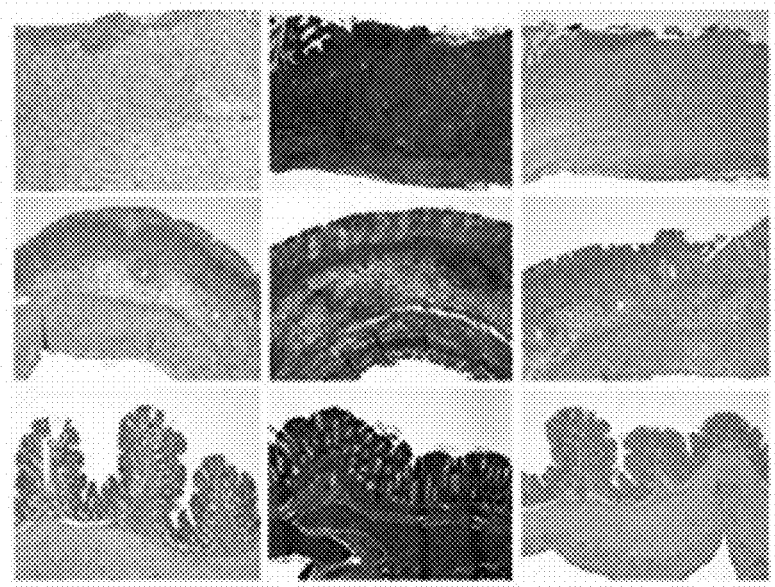
FIG. 2C

FIG. 7A H&E  FIG. 7B Trichrome  FIG. 7C alpha-SMA

| Subject | | 1 | 2 | 3 | 4 | 5 | 6 | 7 |
|---|---|---|---|---|---|---|---|---|
| Fibrosis Score | Stenotic | 3 | 3 | 3 | 3 | 3 | 3 | 3 |
| | Normal | 0 | 0 | 0 | 0 | 0 | 0 | 0 |
| Inflamation Score | Stenotic | 1 | 1 | 2 | 1 | 1 | 2 | 1 |
| | Normal | 0 | 1 | 1 | 0 | 0 | 1 | 0 |
| MM Thickness (μm) | Stenotic | 50 | 50 | 60 | 60 | 80 | 60 | 70 |
| | Normal | 5 | 10 | 10 | 30 | 30 | 20 | 15 |

METHODS AND APPARATUSES FOR MEASURING TISSUE STIFFNESS CHANGES USING ULTRASOUND ELASTICITY IMAGING

CROSS REFERENCE TO RELATED APPLICATIONS

This application is a divisional of U.S. patent application Ser. No. 15/389,036, filed Dec. 22, 2016, which is a divisional of U.S. patent application Ser. No. 14/119,050, filed Nov. 20, 2013, now U.S. Pat. No. 9,554,777, which is the U.S. National Stage of International Application No. PCT/US2012/039179, filed May 23, 2012, which was published in English under PCT Article 21(2), which in turn claims the benefit of U.S. Provisional Patent Application No. 61/489,169, filed on May 23, 2011. The prior applications are incorporated herein by reference in their entirety.

ACKNOWLEDGMENT OF GOVERNMENT SUPPORT

This invention was made with government support under contract no. DK081123 awarded by the National Institutes of Health. The government has certain rights in the invention.

FIELD

The present disclosure relates to novel methods and systems for identifying and measuring tissue stiffness using imaging techniques.

BACKGROUND

In general, the tissue stiffness changes have been important indications of the development of pathological lesions in soft tissues. In past decades, along with other elasticity imaging modalities, such as magnetic resonance elastography (MRE) and magnetic resonance tagging (tMRI), ultrasound elasticity imaging (UEI) or elastography has been developed for measuring, or otherwise evaluating, soft tissue elastic properties. For example, UEI has been utilized in connection with many diseases including (1) thrombus aging/maturational evaluation in human lower limb deep venous thrombosis (DVT), (2) breast cancer diagnosis and screening, (3) differentiation of benign and malignant thyroid masses and cervical lymph nodes, (4) prostate cancer detection, (5) renal transplant graft nephropathy evaluation, (6) cardiovascular diseases, such as characterization of arterial wall stiffness for early atherosclerosis diagnosis, assessment of myocardial wall stiffness for detection of contractile dysfunction, or atheromata assessment for determining vulnerable plaque. (7) liver diseases, such as assessment of the degree of liver fibrosis, and (8) Crohn's disease. Unfortunately, current methods and systems have significant shortcomings that limit or restrict the accuracy and effectiveness of evaluating tissue stiffness changes to identify or recognize the development of pathological lesions in soft tissues.

SUMMARY

Various systems and methods are provided herein for measuring strain applied to and developed in target tissue. As described herein, the strain in target tissue can be measured and standardized. In some embodiments, the measurement of strain in target tissue can be used to assess the non-linearity of the developed strain over a dynamic range.

In a first embodiment, a method of evaluating tissue stiffness of a target area is provided. The method comprises positioning an ultrasound elasticity imaging apparatus adjacent a surface of an area of tissue where the target area is located. A first amount of force can be applied to the area of the tissue to be evaluated to provide a first amount of applied strain on the target area. The force on the strained tissue can be increased until a second amount of force is applied, with the second amount of force providing a second amount of applied strain on the target area. A plurality of ultrasound beams can be directed at the tissue and a plurality of ultrasound echoes can be acquired from the strained tissue in the target area to calculate an amount of developed strain within the target area. The amount of developed strain can be substantially continuously calculated across a strain range between the first amount of applied strain and the second amount of applied strain.

In some embodiments, the amount of developed strain is calculated using speckle tracking data obtained by the ultrasound elasticity imaging apparatus. The developed strain can be calculated at a plurality of amounts of strain across the strain range, such as substantially continuously across the strain range.

In some embodiments, the calculation of developed strain is normalized. The normalization can be achieved by providing an insert between the tissue and a surface of the ultrasound elasticity imaging apparatus. The amount of strain applied to the insert can be calculated using speckle tracking data obtained by the ultrasound elasticity imaging apparatus. The insert can have a thickness that is between about 5 mm and 30 mm, and can be generally ultrasonically transparent. In some embodiments, the insert is between about 10 and 16 mm in thickness.

In some embodiments, the relationship between the amount of developed strain and the amount of applied strain is used to identify a condition of the target area being evaluated, such as Crohn's disease. In some embodiments, the condition identified relates to inflammation, edema development, fibrosis development, or a mix thereof. The condition can comprise, for example, Crohn's disease, ulcerative colitis, a postsurgery site, liver disease (e.g., inflammation vs. cirrhosis), transplant rejection, lymphedema, pancreatitis, and cardiac disease (e.g., acute MI vs. scarring).

The relationship can be depicted graphically and/or by a numerical parameter. The numerical parameter can comprise a nonlinear parameter that is extracted from the relationship between the developed strain and the applied strain.

In another embodiment, a method of using an insert to normalize measurements of tissue obtained by an ultrasound transducer is provided. The method includes coupling an insert to an external surface of the ultrasound transducer. A plurality of ultrasound beams can be directed through the insert and into an area of tissue, and a plurality of ultrasound echoes can be acquired from the tissue and the insert. A measurement of strain on the tissue based on speckle tracking data obtained from ultrasound echoes reflected by the insert can be used to normalize the measurements.

In some embodiments, a first amount of force is applied to the area of tissue to provide a first amount of applied strain on the area of tissue, and the first amount of applied strain on the area of tissue is calculated using speckle tracking. A second amount of force can be applied to the area of tissue to provide a second amount of applied strain on the area of tissue, and the second amount of applied strain on the area of tissue is calculated using speckle tracking. The force can be substantially continuously increased from the application of the first force to the application of the second force, and a varying amount of applied strain on the area of tissue can be substantially continuously calculated from the application of the first force to the application of the second force. A nonlinear parameter can be extracted from the relationship between the developed strain and the applied strain to identify a stiffness characteristic of the area of tissue. In some embodiments, the Young's modulus of the insert can be previously known.

In another embodiment, an insert for normalizing speckle tracking data is provided. The insert can be configured to be coupled to an external surface of an ultrasound transducer, and the insert can have a known Young's modulus and be generally ultrasonically transparent. The insert can have a thickness that is between about 5 mm and 30 mm, and the insert can be sufficiently flexible to deform when coupled to the ultrasound transducer and the insert is brought into contact with soft tissue of a patient. In some embodiments, the insert is between about 10 and 16 mm in thickness.

The foregoing and other objects, features, and advantages of the invention will become more apparent from the following detailed description, which proceeds with reference to the accompanying figures.

BRIEF DESCRIPTION OF THE DRAWINGS

FIG. 2A illustrates gross analysis of distal colon segments.

FIG. 2B illustrates the histology of distal colon sections.

FIG. 2C illustrates a table of histology scoring

FIGS. 7A, 7B, and 7C illustrate tissue histology correlation with UEI strain findings.

DETAILED DESCRIPTION

Figure 1A:
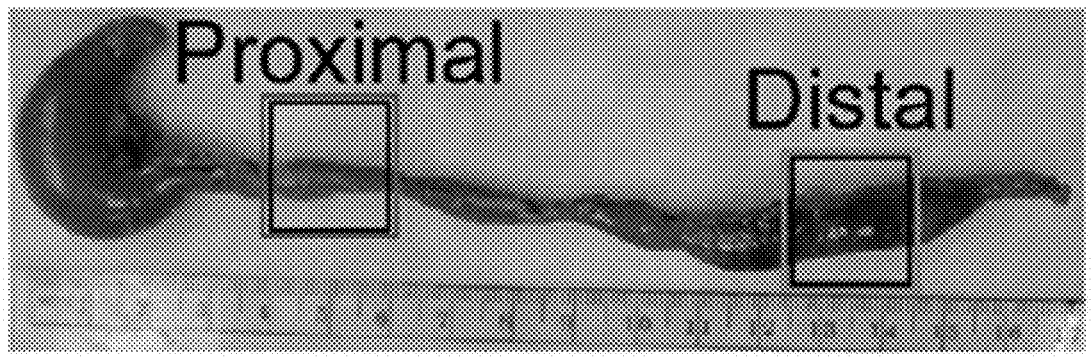
FIG. 1A illustrates the regional effects of a TNBS-ethanol enema on the colon of a subject.

Various embodiments of identifying and utilizing stiffness changes in soft tissue are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Ultrasound Elasticity Imaging for Detecting Intestinal Fibrosis

The following description illustrates systems and methods of using ultrasound elasticity imaging (UEI) to evaluate tissue stiffness that can be indicative of certain conditions or diseases. In particular, the following description illustrates systems and methods of using UEI to identify tissue that is associated with a patient that has Crohn's disease (CD).

Intestinal fibrosis and subsequent stricturing of the intestine in CD can result in substantial patient morbidity and mortality. Fibrostenotic complications are responsible for a significant proportion of hospitalizations, surgeries, and health care costs of Crohn's disease. Immunosuppressive therapies are often successful in treating inflammation in CD, but fail to address pre-existing intestinal fibrosis. Advances in imaging technology, including computerized tomographic enterography and magnetic resonance enterography have improved the assessment of CD extent and activity. However, neither imaging techniques nor blood testing can reliably distinguish fibrotic from inflammatory strictures. Stricture management is a common clinical dilemma, as inflammatory strictures are likely to respond to intensification of medical therapy, but symptomatic fibrotic strictures often require surgical intervention. Symptomatic, non-critical stenoses are often repeatedly treated with hopeful trials of immunosuppressive therapy with little benefit, despite known risks and side effects. Knowledge of stricture composition could aid stricture management, driving medical intensification for inflammation and hastening symptomatic recovery, or limiting exposure to futile, potentially harmful medical therapies by providing an objective indication for surgical intervention.

Ultrasound elasticity imaging (UEI) noninvasively assesses tissue mechanical properties by measuring strain that is developed in the tissue. Strain is the degree of compression of a material in response to a force applied to a fixed area (stress). Materials exhibiting low strain in response to a fixed stress have less compliance, and are commonly described as stiffer or harder. UEI can estimate strain by ultrasound speckle tracking, which is an echocardiographic imaging technique that analyzes motion within an ultrasonic window by tracking interference patterns and natural acoustic reflections.

UEI strain estimates have clearly differentiated abnormal bowel in trinitrobenzene sulfonic acid (TNBS)-treated Lewis rats from normal bowel in the same animal. UEI strain data correlates well to direct mechanical measurement of the tissue elastic properties and histology analysis of tissue. Accordingly, UEI detection of decreased tissue strain is an accurate surrogate marker for intestinal fibrosis.

In the following description, the ability of intestinal UEI to identify the presence and extent of diseased bowel in rats, and to distinguish bowel wall thickening due to predominantly inflammatory versus fibrotic changes is described in more detail. In addition, the UEI technique for the investigation of strictures in Crohn's disease prior to elective surgical resection was performed and the results were compared to mechanical measurement and histopathology.

EXAMPLE 1

Animal Models of Acute Colitis and Intestinal Fibrosis

Acute colitis and colonic fibrosis were generated in Lewis rats by rectal administration of trinitrobenzene sulfonic acid (TNBS) enemas, a well-accepted model of colitis developed by Morris and colleagues. A total of 15 female Lewis rats (Harlan Sprague-Dawley, Inc. IN, 150-180 g) were separated into three groups: acute colitis, chronic intestinal fibrosis, and PBS enema negative controls. Rodents were fasted for 16-24 hours and provided with free access to an iso-osmotic bowel preparation (GoLytely PEG-3350, Braintree Labs, Braintree, Mass.), to eliminate colonic stool prior to catheter insertion for TNBS enemas. Rats were anesthetized with vaporized isoflurane using the drop jar technique. Enemas were administered by placing sedated rodents in a head-down position, inserting a 5 French neonatal feeding tube 6 cm into the rectum, and slowly instilling 250 µL of either TNBS solution or a control solution of phosphate-buffered saline (PBS). The enema tube remained in place for 60 seconds to ensure adequate delivery to the distal colon.

The intestinal fibrosis group received weekly enemas, consisting of TNBS-50% ethanol in a total volume of 250 µL, with escalating weekly TNBS doses over 6 weeks of treatment with 15, 30, 45, 60, 60, and 60 mg TNBS over the course of the experiment. This group was rested 7-10 days prior to UEI scans and sacrifice to allow resolution of acute inflammation from the final enema. The acute colitis group received a single 50% ethanol enema with 15 mg of TNBS; these animals were analyzed by UEI and sacrificed 48-72 hours following enemas so that studies would capture acute inflammatory changes in the colon. Negative control animals received 250 µl PBS enemas in identical fashion to the TNBS animals, weekly for 6 weeks.

During the weekly treatment phase, animals were monitored for health indicators including weight, stool blood, diarrhea, and general activity. After UEI measurement, animals were euthanized by $CO_2$ inhalation after which the colon was resected, opened longitudinally, and stool was removed. Colon weight and length were measured, and the colon was photographed following gross assessment for ulceration, necrosis, and fibrosis. Distal (treated) and proximal (unaffected) sections of colon tissue were resected for histology, protein analysis and mechanical property measurement. Gross effects of treatment enemas were limited to the distal colon, where enemas were delivered. For example, FIG. 1A illustrates the regional effects of a TNBS-ethanol enema. The protocol was approved by the University of Michigan Committee on the Use and Care of Animals (UCUCA) and strictly complied with National Institutes of Health Guide for Care and Use of Laboratory Animals.

Figure 1B:
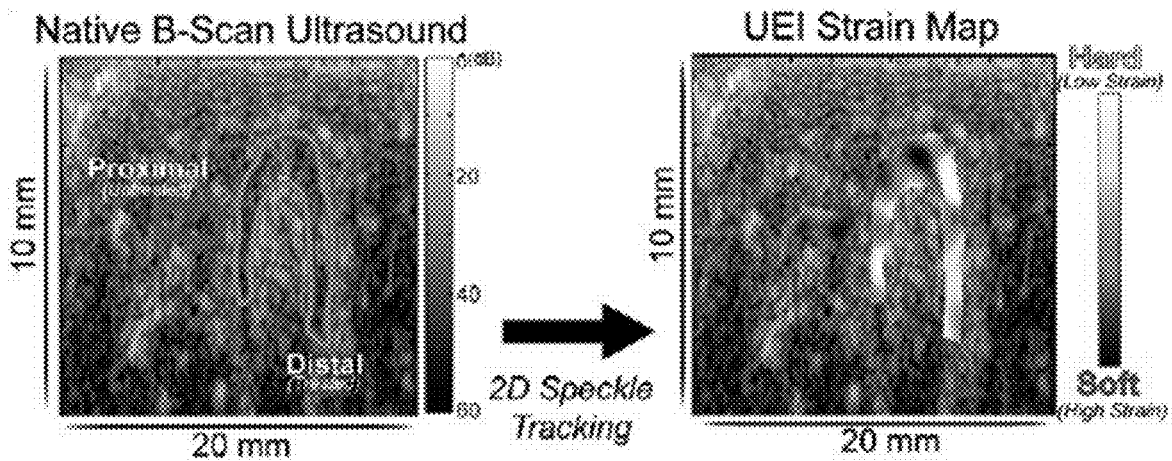
FIG. 1B illustrates how trans-abdominal ultrasound can differentiate diseased and normal rat colon based on anatomic location and evident bowel wall thickening, and a UEI strain map for the region of interest.

At completion of treatment rodents underwent abdominal ultrasound, immediately followed by euthanasia for ex vivo biologic analysis of the colon. Standard ultrasound B-scan images and ultrasound radiofrequency (RF) data were collected using a commercially-available ultrasound scanner (Z-1, Zonare Medical Systems, Mountain View, Calif.) and standard linear array transducer centered at 6.8 MHz, capturing 458 frames at 75 Hz, at a depth of 25-35 mm. FIG. 1B illustrates how trans-abdominal ultrasound can differentiate diseased and normal rat colon based on anatomic location and evident bowel wall thickening. In particular, ultrasound RF data can be captured during transverse plane bowel deformation by compression with the ultrasound transducer and speckle tracking analysis of RF data can be normalized to the average displacement and strain across the entire scan field. FIG. 1B also illustrates a UEI strain map generated for the region of interest.

Before ultrasound analysis, rodents were anesthetized with ketamine (36 mg/kg) and xylazine (3.6 mg/kg). After abdominal fur shaving and application of ultrasound gel, animals were placed supine on a custom built platform below the ultrasound transducer. The transducer was fixed to a crank arm, allowing uniform pressure and displacement to be applied during the six-second abdominal deformation. Prior to deformation, the animals were aligned by centering the ultrasound image over the pubis symphisis, whose inverted "U" structure was readily identified. Following alignment, a mild preload force was exerted on the abdomen cephalad to the symphysis pubis in the transverse plane to push away luminal stool and gas, and reduce shadowing artifacts. Mild preload force does not affect elastic properties of the colon wall. Steady cranking of the transducer towards the abdomen over 6 seconds deformed and compressed the collapsed bowel wall of proximal and distal treated colon, and RF ultrasound data was captured during the deformation. Proximal colon could easily be identified separate from the treated distal colon based on its anatomical location.

EXAMPLE 2

Human Subjects Undergoing UEI

The Institutional Review Board of the University of Michigan approved the study protocol and all participants provided signed informed consent prior to participating in the study. Crohn's disease patients scheduled for elective resection of symptomatic small bowel strictures (n=7) were enrolled. Human subjects underwent trans-abdominal ultrasound using the same ultrasound machine utilized in the animal experiments. Strictures were readily identified in all patients, as investigators utilized existing cross-sectional imaging results, including CT and MRI scans, to guide ultrasound evaluation of the strictures. Upon stricture identification an ultrasound window including the thickened stricture and a loop of ultrasonographically normal bowel were acquired. The crankshaft used to standardize rat luminal deformations was not used in humans, as bowel wall deformations were performed freehand. RF images were captured at 75 Hz over a 6 second bowel deformation, using the transducer to apply abdominal pressure. All scans were performed within 2 days prior to surgery (mean 0.7 days, median 0 days, and range 0-2 days). Immediately following surgical resection, the resected section of stenotic bowel was placed in isotonic saline and sections were taken from representative portions of both stricture and grossly normal tissue for histology and immediate mechanical measurements, as described above.

Comparisons between treatment groups were performed using a paired two-tailed t-test. A difference of the means with P<0.05 was considered significant. Additional methods describing the histopathologic analysis, immunoblotting, ultrasound image processing, and direct mechanical measurements of tissue stiffness are described below.

Histopathologic Analysis of Animal Tissue

Two samples from proximal and distal colon were collected immediately following the UEI procedure. Samples were fixed in 10% buffered formalin, paraffin embedded, underwent H&E, Masson's trichrome, and α-SMA staining, and were assessed by pathologists (DM, BM) in a blinded fashion. Parameters assessed included mucosal, submucosal, and muscularis mucosa thickening, degree of trichrome deposition, degree and type of cellular infiltrate, presence of mucosal ulceration and evidence of necrosis, and overall architectural distortion. Following review of all specimens, a qualitative combination of factors yielded two pathology scores for (a) overall inflammatory and (b) overall fibrostenotic characteristics (scale: 0=none, 1=mild, 2=moderate, 3=severe).

Immunoblotting

Immunoblotting was utilized for the detection of α-smooth muscle actin (α-SMA). Whole tissue was pulverized under liquid nitrogen and lysed in ice-cold RIPA buffer with a cocktail of proteinase inhibitors (Roche, Indianapolis, Ind.). Protein content was determined using a modified Bradford assay kit (BioRad, Hercules, Calif.). Total protein was separated by sodium dodecyl sulfate (SDS) polyacrylamide gel electrophoresis and transferred to PVDF membranes (Amersham Biosciences, Piscataway, N.J.). Membranes were blocked in 5% milk solution for 1 hour at room temperature or overnight at 4° C. α-SMA was detected by incubating the membrane overnight at 4C with mouse anti-human monoclonal antibody (Sigma, St. Louis, Mo.) at 1:5000 dilution in 5% milk/TBST. As a loading control, a mouse antibody for GAPDH (Chemicon, Temecula, Calif.) was used. Secondary antibody anti-mouse IgG HRP (Amersham, Piscataway, N.J.) was incubated for one hour at room temperature and the signal was detected by the Pierce detection system (Rockford, Ill.).

Ultrasound Image Processing for UEI Strain Estimates

Two-dimensional sections of distal (treated) and proximal (untreated) colon regions of interest (ROI) were identified by a clinical ultrasound expert in the original B-Scan images. Strain estimates were generated off-line by processing RF data using phase-sensitive correlation-based two-dimensional speckle tracking algorithms which calculated the in-plane frame-to-frame axial and lateral displacement. The normalized strains were determined from the mean strain developed in the ROI (where correlation coefficient of 2D-speckle tracking is greater than 0.9) divided by the magnitude of the applied mean strain averaged over imaging area (excluding ROI) where correlation coefficient of 2D-speckle tracking is greater than 0.9 within the linear tissue elastic region of less 15% of strain. Negative strain values represent tissue compression while positive values reflect expansion. Strain ratio is the average strain of the distal colon divided by the average strain of the proximal colon.

Direct Mechanical Measurements

Figure 1C:
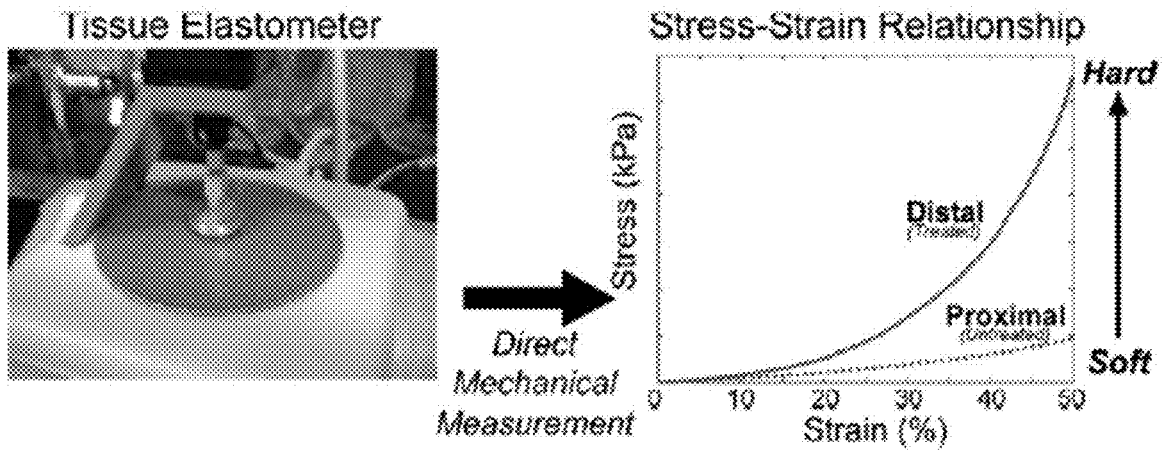
FIG. 1C illustrates a tissue elastometer that can be used to measure direct mechanical properties and an exemplary stress-strain relationship.

Tissue sections from distal and proximal colon were cut into 1 cm by 1 cm squares for immediate, direct mechanical measurement using an elastometer (MicroElastometer, Artann Laboratories, West Trenton, N.J., USA). The thickness of the samples ranges from 1.0 mm to 4.0 mm. The elastometer is comprised of a pressure-sensitive stage and a piston which applies incremental force to the sample on the stage. By measuring vertical tissue displacement, and incrementally applied compressive force on the tissue surface, the elastometer reports stress (force per unit area) and strain (resulting compression) of the tissue sample. The stress-strain relationship is used to derive the elastic modulus, known as the Young's Modulus (YM), which is an expression of hardness or stiffness of a material. The derived YM of the tissue sample was based on the stress-strain relation, estimated as the slope of the relation by linear curve fitting (first order polynomial fit) in a linear range of 7.5% to 15% in this study18. Given variability in rat size, weight and girth, distal (affected) colon tissue YM measurements were normalized to the YM of the intra-animal proximal colon, yielding a Young's Modulus ratio. FIG. 1C illustrates a tissue elastometer that can be used to measure the direct mechanical properties of a stress-strain relationship (also shown in FIG. 1C).

Results

Examples 1 and 2

Acute TNBS Enemas Induce Inflammatory Colitis, while Chronic TNBS Enemas Induce Colonic Fibrosis in Rats The objective of the animal portion of our study was to determine if UEI measurements of the rat colon could distinguish inflammatory and fibrotic causes of bowel wall thickening. Biologic confirmation of the fibrotic and inflammatory phenotypes was performed by gross pathologic, histologic, and molecular methods. At sacrifice, gross colon morphology was consistent with inflammation and fibrosis. As shown in FIG. 2A, gross analysis reveals thickened and stiff distal colon segments in the chronically treated group (upper panel), while gross edema, hemorrhage, necrosis, and soft tissue is found in the acute colitis group (middle panel). The acute TNBS colitis group demonstrated distal colon thickening with areas of hemorrhagic necrosis and a subjectively soft texture. The chronic TNBS group also had distal colon thickening, but its texture was hard and rigid. The chronic TNBS group colon length was shorter compared to the control and inflammation groups. As shown in the lower panel of FIG. 2A, the distal colon of control animals which received PBS enemas was grossly unremarkable.

Gross pathological effects were limited to the extent of TNBS instillation in the distal colon; the proximal colon was normal in all rat groups. Colon density (mass/length), was significantly greater in the chronic fibrosis rat group (0.24±0.065 g/cm2), compared to the acute TNBS-colitis model (0.18±0.018 g/cm2), P=0.047 (data not shown). While the chronic fibrosis group's normalized colon weight differed from PBS-control rats (0.16±0.045 g/cm2), P=0.006, the average acute TNBS-colitis rat colon tissue weight did not significantly differ from the controls.

Histology review of tissue sections from distal colon in acute and chronically TNBS treated animal groups revealed changes indicative of acute colitis and intestinal fibrosis phenotypes, respectively. As shown in FIG. 2B, thickening of the mucosa and submucosa was evident in both the groups. However, Masson's trichrome staining showed substantially more collagen deposition in the chronic fibrosis group (upper panel), while mucosal thickening in the acute inflammatory group (middle panel) was associated with edema and an inflammatory cellular infiltrate with little change in collagen distribution. An inflammatory infiltrate was present in both TNBS rat groups, but was more prominent in the acute inflammatory group. Mucosal ulceration was present in both the acute inflammatory and the chronic fibrosis groups, but only the acute group demonstrated patchy regions of necrosis. Finally, substantial thickening of the muscularis mucosa was revealed by α-smooth muscle actin (α-SMA) staining and prominent architectural distortion in the chronic fibrosis group. In summary, acute and chronic TNBS treatment of the rat distal colon consistently produced phenotypes consistent with acute colitis and chronic intestinal fibrosis in the rat distal colon, while the proximal colon remained unaffected as shown in the histology scoring for all animals shown in FIG. 2C. Overall, chronic fibrosis rats demonstrated histologic changes comparable to human fibrostenotic strictures in inflammatory bowel disease, while the acute inflammatory group showed characteristics of acute colitis without fibrotic changes.

Figure 2D:
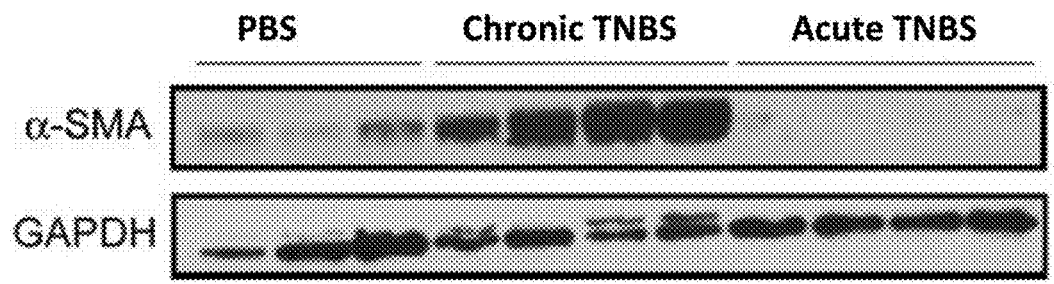
FIG. 2D illustrates Western blotting of colonic extracts.

Western blotting for α-SMA, a marker of tissue fibrosis, was dramatically induced in the chronic fibrosis group compared to both PBS controls and acute colitis control groups, suggesting activation of myofibroblast fibrogenesis in the chronic fibrotic model compared to the acute inflammatory model and PBS control rats. FIG. 2D illustrates western blotting of colonic extracts for α-SMA, with GAPDH protein expression used as a loading control.

In summary, chronic fibrosis rats demonstrated greater colonic mass and density as well as histopathology and protein expression characteristic of human fibrostenotic strictures.

Figure 3:
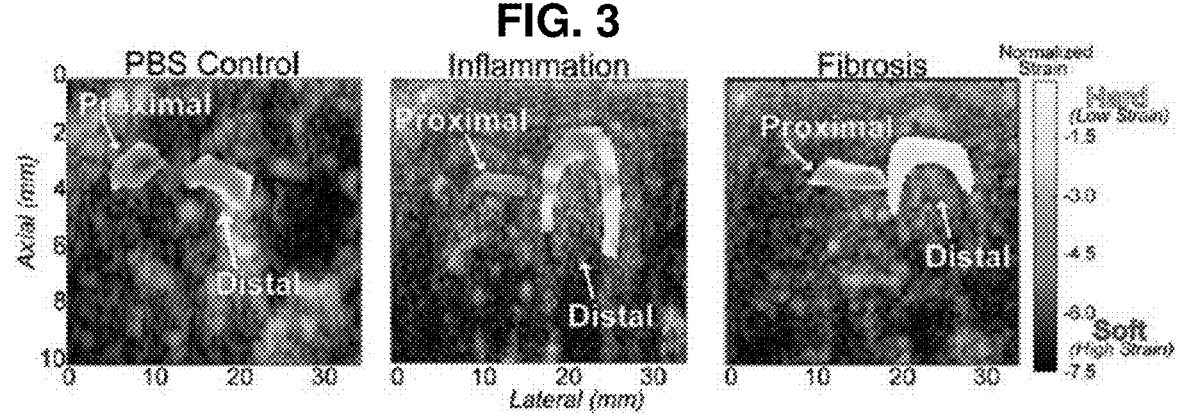
FIG. 3 illustrates UEI strain measurements that can distinguish inflammatory from fibrotic thickened colon in TNBS-treated rats.

UEI Strain Measurement Distinguishes Inflammatory from Fibrotic Thickened Colon in TNBS-Treated Rats Proximal and distal segments of colon were identified in anesthetized rats by transabdominal ultrasound. Distal colon segments from inflamed and fibrotic groups exhibited wall thickening compared to their proximal colons, and to the distal colons of negative control rats. Ultrasound elasticity imaging was used to measure the bowel wall strain in distal (affected) and proximal (unaffected) colon. FIG. 3 illustrates UEI strain measurements that can distinguish inflammatory from fibrotic thickened colon in TNBS-treated rats.

Low strain values indicate hard tissue with limited deformation; high strain indicates soft, deformable tissue. Mean UEI normalized strain was lowest (hardest) in the distal colon of the chronic fibrosis group, −1.10±0.167, highest (softest) in the distal colon of the negative controls −3.57±0.352, and an intermediate mean strain was found in the acute inflammation group −2.07±0.717. The UEI normalized strain differed between the negative control group and the acute inflammation group (P=0.015), and also between the negative control group and the chronic fibrosis group (P=0.001). A significant difference in UEI strain was also found between the acute inflammation and chronic fibrosis groups (P=0.037). Given the possible variation in both trans-abdominal force applied and individual rat anatomy. The UEI strain ratio in the chronic fibrosis group measured −0.43±0.09, PBS negative control group was −0.87±0.07, and −0.54±0.09 in the acute inflammation group. The UEI strain ratio differed significantly between the chronic fibrosis and the acute inflammation groups, P=0.030.

Figure 4:
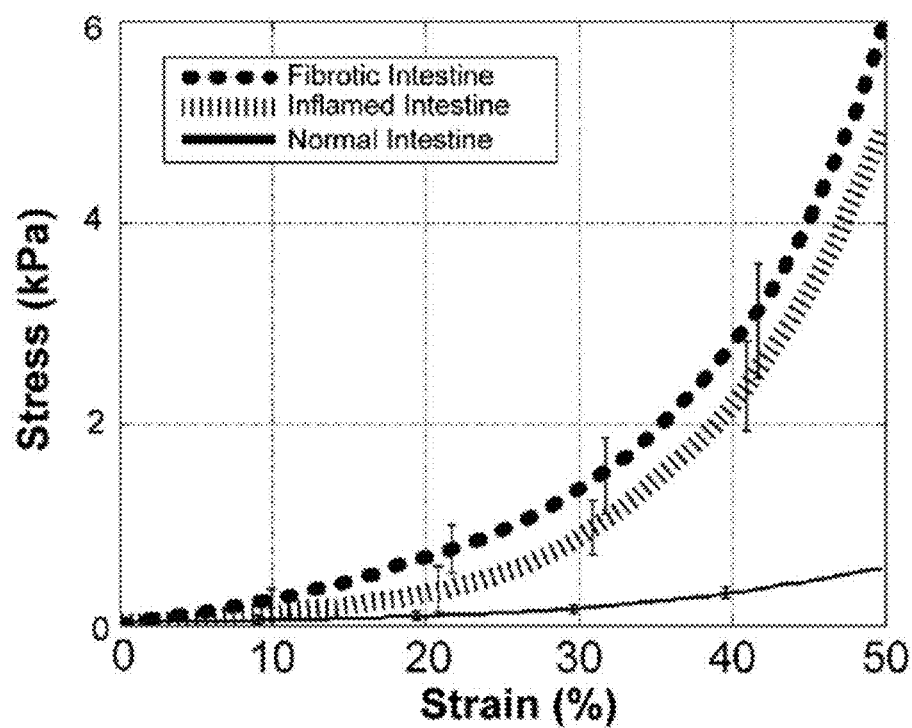
FIG. 4 illustrates how direct measurement of colon mechanical properties correlates with UEI strain in rats.

Direct Measurement of Colon Mechanical Properties Correlates with UEI Strain in Rats UEI strain non-invasively measures the mechanical properties of tissue. Microelastometer measurements of ex vivo colon tissue samples measure the stress-strain relationship of the tissue, and the slope of this curve represents Young's Modulus of the tissue (YM). High YM indicates rigidity, or hardness; it is therefore inversely correlated with strain. Stress-strain curves of the distal colon samples from all rat groups demonstrated that YM was highest (2.75±0.56 kPa, hardest) in chronic fibrosis group, lowest (0.30±0.25 kPa, softest) in the PBS negative control group, and intermediate (2.16±0.40 kPa) in the acute inflammation group FIG. 4 illustrates how direct measurement of colon mechanical properties correlates with UEI strain in rats. Direct measurement of the tissue mechanical properties from distal rat colon were made using a microelastometer. The material characteristics measured noninvasively by UEI reflect the mechanical properties of rat intestine. Fibrotic tissue had the highest YM (stiffest) 3.44±1.50 kPa; normal tissue had the lowest YM (softest) 1.03±0.15 kPa; and inflammatory tissue had intermediate stiffness of 2.50±0.70 kPa (in a linear range of 7.5% to 15% strain). These values were normalized to the right colon measurement of Young's modulus, and the paired differences between all 3 groups were statistically significant fibrotic vs. inflamed, P=0.024; Inflamed vs. control, P=0.042; fibrotic vs. control, P=0.035. Averaged stress-strain curves with errors bars showing standard deviation.

Proximal colon measurements were similar across groups with a mean YM of 0.92 kPa with a range of 0.49-1.15 kPa. The mean normalized YM ratio (distal divided by proximal colon YM) for chronic fibrosis, acute inflammation, and PBS negative control groups were 6.57, 3.07, and 1.18, respectively. All differences between these three groups were statistically significant (fibrosis vs. inflammatory, P=0.024; inflammatory vs. control, P=0.042; fibrosis vs. control, P=0.035).

UEI Strain Measurement Distinguishes Normal Bowel from Fibrotic Bowel in Human Subjects with Crohn's Disease Pre-operative transcutaneous ultrasound scans were performed in 7 human subjects using the same ultrasound device and 2-D speckle tracking algorithms as in the rat experiments. In human subjects, the scanning plane included both diseased stenotic bowel and an adjacent loop of apparently unaffected small intestine (with a non-thickened bowel wall). Deformation using the scanning transducer was performed manually on supine patients, and off-line image processing was used to generate UEI strain maps.

Figure 5:
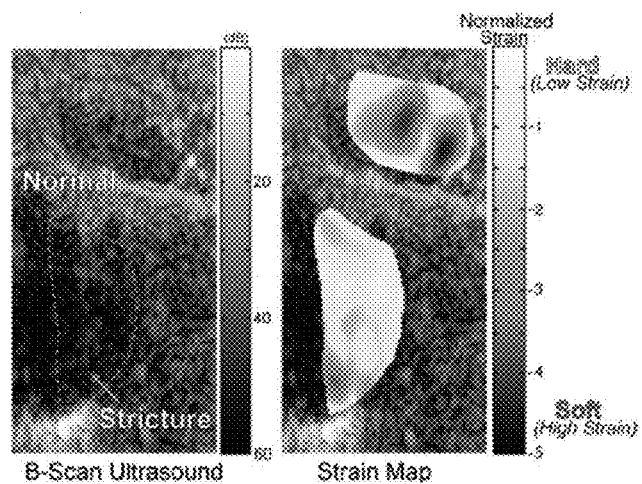
FIG. 5 illustrates representative ultrasound B-scan image of a Crohn's disease subject with symptomatic small bowel stricture (left panel), outlining the regions of interest (ROI) for the stricture and adjacent normal appearing bowel.

FIG. 5 illustrates representative ultrasound B-scan image of a Crohn's disease subject with symptomatic small bowel stricture (left panel), outlining the regions of interest (ROI) for the stricture and adjacent normal appearing bowel. The corresponding UEI normalized strain map is presented, right panel. Across seven subjects, the mean UEI normalized strain in stenotic bowel was −0.87±0.22. Adjacent normal appearing bowel was significantly softer, −1.99±0.53 (P=0.0008).

Figure 6A:
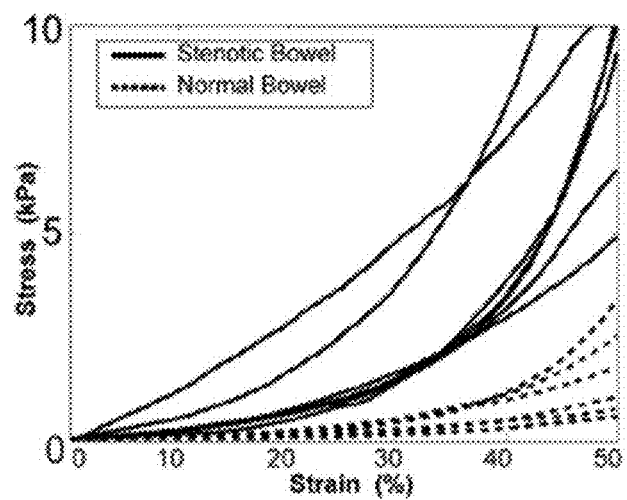
FIG. 6A illustrates direct mechanical measurement of tissue samples from subjects with Crohn's disease.
Figure 6B:
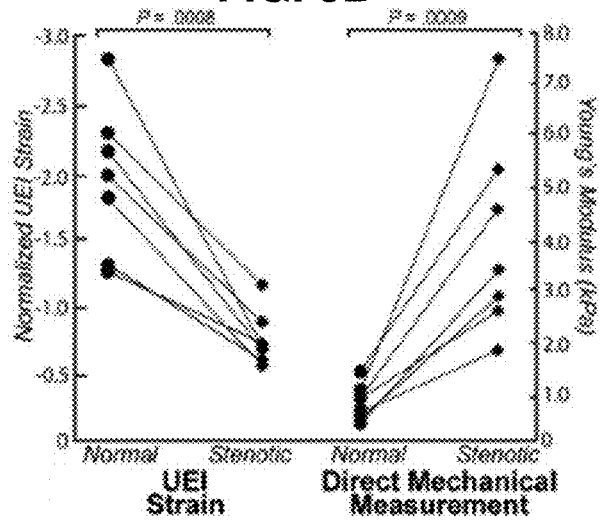
FIG. 6B presents the correlation between ultrasound strain measurement and direct mechanical measurement.

Direct Measurement of the Mechanical and Biologic Properties of Ex Vivo Small Bowel Tissue Samples Correlated with UEI Strain in Human Small Intestine Tissue from stenotic and adjacent normal appearing small bowel resection margins underwent immediate direct measurement of tissue mechanical properties using the tissue elastometer. Direct mechanical measurement of tissue samples from Crohn's subjects plotted as stress vs. strain revealed fibrostenotic sections of bowel were clearly more stiff (mean YM 4.14±1.88 kPa) than the grossly normal tissue resection margins (mean YM 0.96±0.25 kPa) in all subjects, P=0.0009 (FIG. 6A). Strain and stress are inversely proportional mechanical properties, with low strain and high stress both indicates stiffness (hardness). Plotting UEI strain and Young's Modulus of normal and stenotic bowel with lines connecting individual subjects, UEI strain and direct mechanical measurement are appropriately inversely correlated, r=−0.81 (FIG. 6B). The noninvasive transcutaneous UEI measurements are accurate estimates of the true tissue mechanical properties of intestine.

Accordingly, the Young's modulus in stenotic tissue was significantly harder (mean 4.14±1.88 kPa) than that of the (grossly normal) tissue from the surgical resection margin (mean 0.96±0.25 kPa), P=0.0009. Variability of stiffness in the stenotic tissue was expected resulting from differences in biologic disease severity, unavoidable variation in specimen sectioning, and heterogeneity of stiffness within the section itself. As in the TNBS rats, noninvasive transcutaneous measurement of tissue strain by UEI accurately measured the ex vivo mechanical properties of the resected small intestine in Crohn's disease.

FIG. 7 illustrates tissue histology correlation with UEI strain findings. Histology assessment of ex vivo stenotic and grossly normal small bowel margins confirmed that the strictures were predominantly fibrotic, and the grossly normal resection margins lacked major inflammatory or fibrotic changes. Histology of normal human bowel (upper panel) from resected margins, compared to stenotic human bowel (lower panel) stained with hematoxylin and eosin (FIG. 7A), Masson's trichrome (FIG. 7B), and alphasmooth muscle actin (FIG. 7C) stains (5× magnification). Scale bar represents 1 micron and the inset shows a 50× magnification, detailing changes in the muscularis mucosa thickness (as shown by the vertical black bar). As shown in FIG. 7D, the histology scoring shows predominantly fibrotic changes with minimal inflammation in the strictures.

Figure 7D:
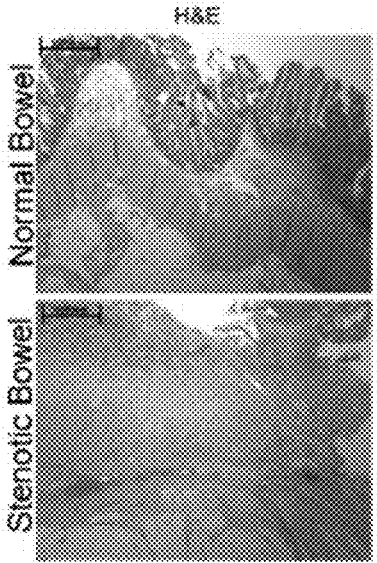
FIG. 7D illustrates the correlation between ultrasound strain measurement and direct mechanical measurement.
Figure 7D:
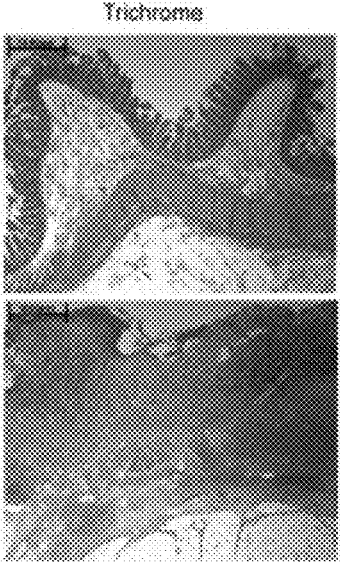
Figure 7D:
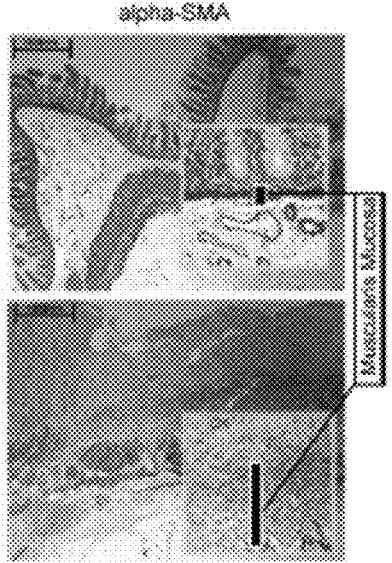
Figure 7E:
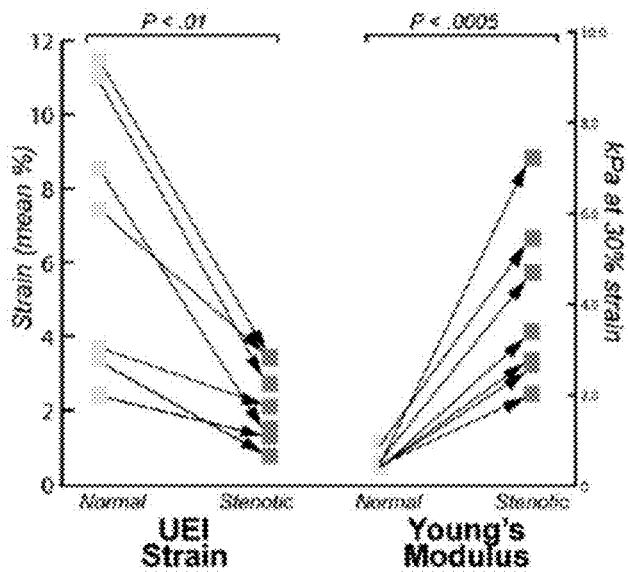
FIG. 7E illustrates UEI strain measurements of direct measurement of elastic modulus in ex vivo bowel from persons suffering from Crohn's disease.

FIG. 7E illustrates UEI strain measurements of direct measurement of elastic modulus in ex vivo bowel from persons suffering from Crohn's disease. UEI strain measurements in human subjects correlate with direct measurements of tissue mechanical properties. Immediately following surgical resection, samples of stenotic resected intestine and apparently normal tissue resection margins underwent direct measurement of their elastic modulus using the tissue elastometer (left panel). Fibrostenotic sections were clearly harder (mean 4.14 kPa, SD±1.88) than the grossly normal tissue resection margins (mean 0.96 kPa, SD±0.25) in all subjects, p<0.0001. The mean UEI strain was decreased in the fibrotic segment (3.61%, SD±1.57) compared to the tissue at the resection margin (8.95% SD±5.02), demonstrating the relative hardness of the stenotic tissue by UEI strain, p<0.02. Strain and stress are inversely proportional mechanical properties, with low strain and high stress both indicates stiffness (hardness). The UEI strain estimates and the direct mechanical measurements are appropriately inversely correlated, r=0.81 (right panel). The noninvasive transcutaneous UEI measurements are accurate estimates of the true tissue mechanical properties of intestine.

Stenotic tissue demonstrated significant architectural distortion, mucosal and submucosal expansion, and evidence of submucosal collagen deposition. The stenotic tissue was not purely fibrotic, containing mild and occasionally moderate inflammatory cellular infiltrates. In addition, some resection margins demonstrated mild inflammatory changes, possibly harboring active inflammatory bowel disease, but no evidence of fibrosis was found in these samples. By pathologic grading, all of the stenotic tissue samples demonstrated severe fibrotic changes while normal tissue displayed no fibrosis and minimal inflammatory changes.

Additional Discussion Regarding Results

Examples 1 and 2

The monitoring and management of inflammation in IBD have undergone revolutionary advances in the past 20 years, but the development of methods of detection and treatment of fibrosis in Crohn's disease have lagged behind. Fibrostenotic complications lead to frequent hospital admissions, surgical interventions, and substantial costs in Crohn's disease. Conventional treatment of fibrosis is limited to preventive, anti-inflammatory strategies. Anti-fibrotic therapies for other organs may hold promise for intestinal fibrosis. Accordingly, systems and methods to identify and quantify intestinal fibrosis in vivo provide a significant physiological surrogate endpoint in the monitoring of chronic Crohn's disease.

Accordingly, mechanical properties of intestine can distinguish normal from fibrotic intestine in a chronic TNBS rat model of IBD and noninvasive transcutaneous ultrasound elasticity imaging (UEI) can reliably detect changes in tissue mechanical stiffness. In addition, UEI can differentiate inflammatory from fibrotic intestine in TNBS rat models of IBD and can be performed with similar results with humans. Moreover, transcutaneous UEI accurately measures the tissue properties of stenotic segments of bowel in patients with Crohn's disease when compared to the gold standard of tissue elastometry. RF speckle tracking data can be processed off-line with specialized algorithms or it can be performed using a real-time approach.

In the above examples, it was assumed that the ultrasonographically normal bowel adjacent to stenotic intestine in the human UEI studies was truly normal; however, it could have been affected by changes related to Crohn's disease. For example, if inflammation in the apparently "normal" adjacent bowel occurred, this would be expected to reduce the UEI accuracy. The examples of UEI described above were used only to evaluate known stenotic lesions localized on cross-sectional imaging as it would be impractical to use UEI to search the entire bowel for stenosis. UEI will likely be most valuable for the focused evaluation of known lesions.

In following Crohn's disease patients over time, the value of repeated CT enterography is limited by radiation exposure, and the value of repeated MR enterography by cumulative cost. For longitudinal monitoring of Crohn's disease patients at high risk of complications, the combination of contrast or Doppler-enhanced ultrasound for the evaluation of intestinal inflammation, and UEI for the evaluation of intestinal fibrosis, could be an attractive option. As this was a cross-sectional study, we measured only severe Crohn's intestinal stenosis requiring surgery. However, our animal model data demonstrates that UEI technology can distinguish intestinal inflammation from fibrosis using transcutaneous ultrasound data.

Accordingly, UEI can be applied to differentiate inflammatory from fibrotic changes in Crohn's disease, aiding clinicians in medical and surgical decision-making. UEI can also provide longitudinal information on the natural history of Crohn's disease, including identifying and following high-risk patients who develop early fibrosis and rapidly progress to fibrostenotic strictures. Finally, as a reliable, non-invasive means of distinguishing and quantifying fibrosis, UEI represents an important tool in evaluating candidate anti-fibrotic therapies for Crohn's disease.

Non-Linear Parameters in Strain-Strain Relation of the Soft Tissues and its Application in UEI An assessment of the non-linearity of strain can further improve the discriminant power of UEI in connection in detecting the early stages of intestinal fibrosis or other more subtle tissue changes.

Pathologically hardened tissues can be distinguished from the normal surrounding soft tissue as described herein. In the examples described above, the in-vivo measurements of strain from UEI correlate well with histology and direct ex-vivo mechanical measurements of elastic modulus, and demonstrate that the UEI approach can detect stiffness changes as a result of fibrosis development with high sensitivity and reproducibility. However, differentiating subtle changes in stiffness can be significantly more difficult due to the limited sensitivity of elasticity imaging techniques.

Crohn's disease is an inflammatory bowel disease that is often difficult to diagnose by physical examination as its symptoms are similar to those of other intestinal disorders, such as irritable bowel syndrome and ulcerative colitis Inflammation occurs in episodic flares in CD, which are part of the waxing and waning course of the disease. Healing between flares allows the intestine to reconstitute its epithelium, but this healing process results in the deposition of fibrotic scar tissue. Repeated cycles of flares and healing often lead to clinically significant fibrosis and stenosis of the intestine, requiring surgery in 20% of patients within 3 years of diagnosis, and in 57% of patients after 10 years of disease. This has a substantial impact on quality of life and medical costs.

When Crohn's patients have abdominal pain and vomiting, this often indicates severe narrowing or stricture of the small intestine. This can be due to inflammation which can be treated with medical therapy, due to chronic fibrosis which requires surgery, or due to a mixture of the two. Differentiating fibrotic and edematous thickening of the bowel wall is important for diagnosis and follow-up treatment. This is because it is desirable to avoid operating on an inflammatory stricture since many patients with Crohn's disease develop complications secondary to the surgery. With regard to treatment, fibrotic strictures generally do not respond to the powerful anti-inflammatory agents given for inflammatory strictures.

From our observations with the TNBS treated rat model, there are only the subtle differences in stiffness between acute and chronic stages, making it very challenging to differentiate edematous from fibrotic tissues. However, the causes of the wall thickening and stiffness are different in the two circumstances. Acute inflammatory wall thickening is due to inflammation with a high water content, as opposed to fibrotic-tissues, which are thickened because of scar formation. During the initial stages of a deformation, the edematous tissue might generate high strain (softer) until the water contents are forced out and low strain (stiffer) subsequently. Therefore, although a stiffness assessment by conventional UEI may not be able to differentiate the edematous from fibrotic tissues with the strain measured at a single-point of deformation, the nonlinear characteristics over a large strain dynamic range of the edematous tissue may be able to make this distinction. These characteristics may be used to identify the stage of lesion development.

Analyzing the developed strain inside a targeted lesion over a relatively large dynamic range of the applied strain to the body of a patient (e.g., animal) can provide significant advantages. The following methods and systems evaluate the nonlinear characterization of tissue stiffness change using UEI for providing an improved model for analyzing tissue.

A finite element based soft tissue model (FEM) was generated to simulate the relation between the developed strain inside the targeted inclusion and the applied strain within the range of elastic modulus of the tissue in the animal model. Based on the developed strain-to-applied strain (also referred to as strain-to-strain herein) relations from the simulation, an analytical equation adapted from the Hill equation was provided and the related nonlinear parameters were optimized for the simulation results. As described in more detail below, the techniques described herein can identify subtle stiffness changes, such as those related to acute inflammation and fibrosis in an animal model. The strain-to-strain relation and/or the extracted nonlinear parameter can be empirically optimized to the in vivo measurements to successfully differentiate edematous bowel from the surrounding normal or chronically fibrosed bowel.

EXAMPLE 3

Animal Model

A total of 8 female Lewis rats (Harlan Sprague-Dawley, Inc., and weights in 150~180 g) were separated into two groups of acute colitis and chronic intestinal fibrosis. Chronic intestinal fibrosis in Lewis 4 rats was induced with escalating weekly doses of TNBS over 6 weeks. Acute inflammation was induced in Lewis 4 rats with a single TNBS-ethanol enema based on a well-known model of colitis developed by Morris and colleagues. The proximal colons were normal in each of these rats and could be used as controls. There were, therefore, 8 normal bowel segments. The protocol was approved by the University of Michigan Committee on the Use and Care of Animals (UCUCA) and strictly complied with National Institutes of Health Guide for Care and Use of Laboratory Animals. Further details of TNBS treatments are described in the previous study.

Ultrasound RF Data Collection

In vivo ultrasound in-phase/quadrature (I/Q) data were acquired at a frame rate of about 60 frames per second (depending on depth) by using a linear ultrasound probe (L10-5, centered at 6.5 MHz, ZONARE Medical System, Mountains View, Calif., USA) connected to a commercial ultrasound scanner (Z. one Ultra sp Convertible Ultrasound System, ZONARE Medical Systems, Mountains View, Calif., USA). Ultrasound data sets were continually collected while the abdomen was being pushed by the ultrasound probe to develop about 10% average strain over a total of 3 seconds. The animals were anesthetized with ketamine (36 mg/kg) and xylazine (3.6 mg/kg) during the exam. The ultrasound probe was placed on the anterior abdomen wall of the rats, and was also used to compress the rat's abdominal wall and underlying tissue. A mild preload on the abdomen in the transverse plane was used to displace luminal stool and gas while reducing image shadowing artifacts. The transducer was fixed to a laboratory designed deformation device to produce a uniform displacement on rat's shaved abdomen. The overall experimental setup is similar to the examples described above.

Phase-Sensitive Two-Dimensional (2D) Speckle Tracking for Strain Estimates

The beam-formed I/Q data were derived from the raw data stored in the scanner's channel domain memory. Radio frequency (RF) data samples were reconstructed from the IQ data considering the time-frequency compensation parameters and sound speed to improve the data quality. A phase-sensitive correlation-based 2D speckle tracking algorithm was then applied to the reconstructed RF data to estimate the displacement between each frames. Frame-to-frame displacements were estimated from the position of the maximum 2D correlation function of the baseband complex signals derived from the RF data. The search kernel of the speckle tracking was set to be about ultrasound speckle size. The ultrasound speckle size was estimated to be 0.25 mm in axial direction and 0.5 mm in lateral direction from the 2D correlation function of the baseband signals. The frame-to-frame displacements were then accumulated over a number of frames covering the entire deformation to estimate the total displacements with enhanced the signal to-noise ratio (SNR). The axial normal strains were then calculated by taking the spatial derivative of the accumulated axial displacements with respect to the axial direction using the centered numerical differentiation.

As accumulated axial strains changing with number of US frames were determined, the region of interest (ROIs) for normal/fibrotic areas or normal/acute, and the reference of the rat's pelvis were marked by a clinical ultrasound expert in the original B-Scan images. The corresponding ROIs were used to obtain the developed strains by averaging strains over the whole ROIs for normal/acute/chronic groups, the relationships between the developed strain and number of US frame were determined from the accumulated axial strain maps for every acquired RF sequence. The overall averaged strain estimated from the pelvis or spine during a deformation is used to represent the applied average strain based on the assumption that the tissue overlying the pelvis or the spine is generally similar from animal to animal. At every number of US frame, an overall strain for every scan was determined from the rat's pelvis displacements and initial position obtained from the B-scan image, the overall strain was used as an applied strain for every scan, the relationships between the applied strain and number of US frame were determined from the B-scan image sequences.

Normalized strains for normal/acute/chronic were determined from the developed strain over the ROI divided by the applied strain at number of US frames usually around 50 or overall developed strain less than 15% in the linear range.

Direct Mechanical Measurements

The tissue samples (both normal and treated bowel for every rat) were harvested after the IQ data collection and B-scan ultrasound imaging (for representative images for the rats). A commercial soft tissue compression test device (MicroElastometer, Model 0501, Artann Laboratories, Lamberville, N.J., USA) was used to measure the elastic modulus of the excised normal bowel and treated bowel samples. The device measures the displacement vs. applied force when a test sample is under of compression. The applied force is measured by a strain gage (Acculab VI-200, Acculab, Edgewood, N.Y., USA) mounted under the object plate. The measurable force range is up to 2N with a precision of 0.1 mN. The device employs a pressing stamp with a rectangular cross-section of 8.88 mm by 3.98 mm. The position of the compression stamp is controlled by a hybrid linear actuator (HIS 35N67-12-405, Haydon Switch & Instrument Inc., Waterbury, Conn., USA). The travel distance per step was set for 3 μm. Each sample was measured twice for statistical analysis. Between each measurement, the sample was soaked in saline water for a few minutes to allow it to regain its elasticity. The test samples were cut into 10 mm by 10 mm with height varying from 1 mm to 4 mm (average value 2.8 mm±1.5 mm from all 32 samples for 8 rats).

Histology

The tissue samples from the distal colon for 8 rats were collected immediately following the ultrasound RF data acquisition. The harvested tissue samples were dissected into two 10 mm by 10 mm pieces for direct mechanical measurements and histology. Samples for histology were put into 10% buffered formalin, paraffin embedded, underwent hematoxylin and eosin (H&E), trichrome, and a-smooth muscle actin (SMA) staining, and assessed by pathologists. The process for histology is detailed in our previous study.

Finite-Element Based on Nonlinear Soft Tissue Model

Figure 8:
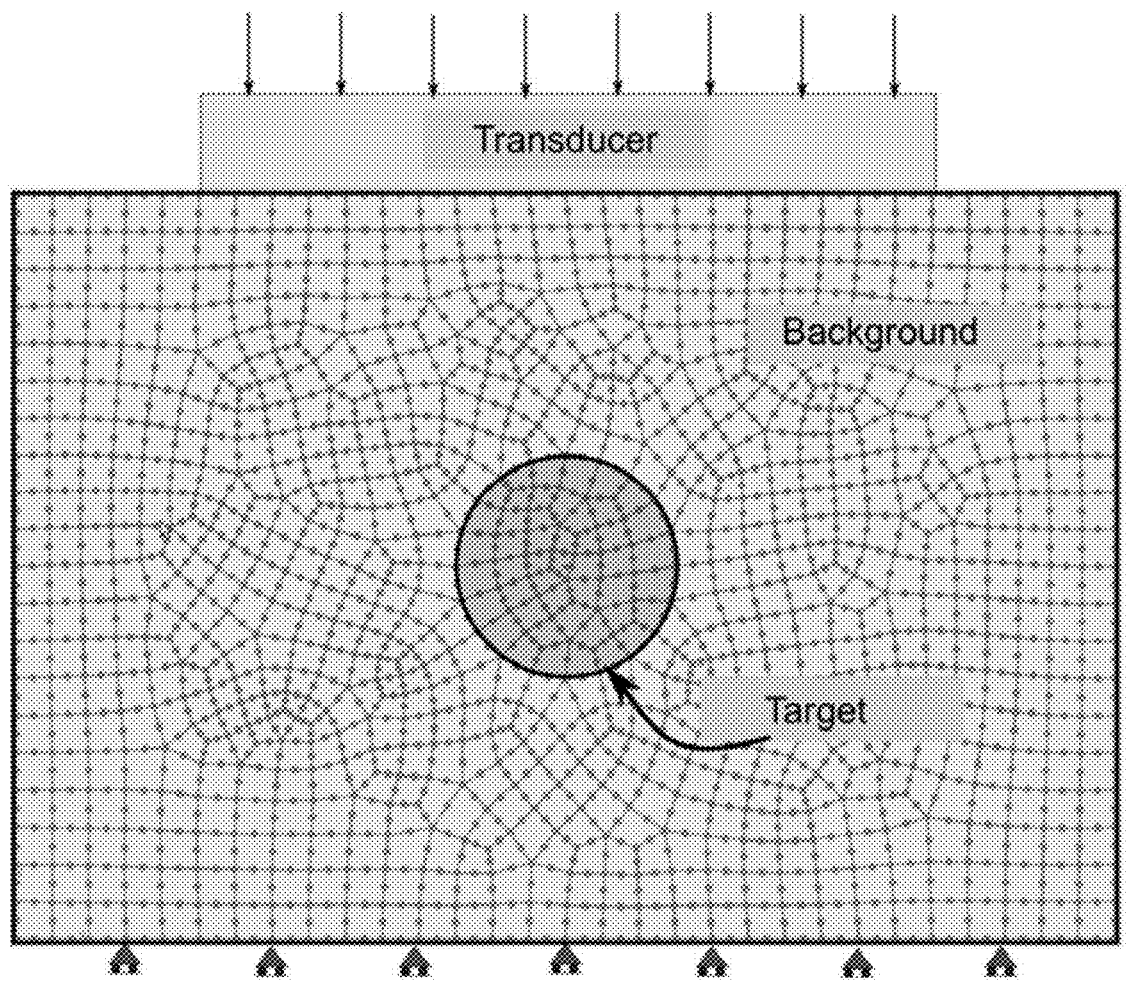
FIG. 8 illustrates a 2-D plane strain for numerical phantoms of the representative cases of soft, medium and hard inclusions.

To numerically simulate the relation between the developed strain of the target inclusion and the applied average strain, a simple finite element (FE) based nonlinear soft tissue model was developed using a commercially available software package (ABAQUS, Dessault Systems, Rhode Island, United States). FIG. 8 presents the schematic of the FE model. A circular inclusion in a uniform rectangular tissue block is modeled, while a rigid transducer was used to deform the sample with equal displacement boundary conditions (DBC). An infinitely long cylindrical inclusion of diameter of 12.7 mm is embedded in a homogeneous block of 60 mm by 40 mm (in Height). The tissue block is quasi-statically deformed by an ultrasound probe with width of 40 mm in the middle of the upper surface by applying an equal displacement boundary condition on the top of the background block.

The 2 dimensional (2D) plane strain problem was solved quasi-statically using 40 steps to obtain a total axial displacement of 8 mm out of the initial height of 40 mm, which results in is 20% total strain with 0.5% strain for each deformation step. The boundary condition at the bottom surface was set as roller ($u_y$=0; no axial displacement, please note x and y in FIG. 8) and all other surfaces were set as free. The contact between the surface of the transducer and top surface of the block was 'tied'—no relative motion between the surfaces was allowed. The same condition was applied for the contact surface between the inclusion and the surrounding tissue block. The model was meshed using regular 8-noded plane stain elements with reduced integration.

A hyper-elastic nonlinear material model is employed for the background material surrounding the target inclusion. The polynomial which has been widely used in modeling soft tissues like breast was used as follows:

$$U = \sum_{i+j=1}^{N} C_{ij}(I_1 - 3)^i (I_2 - 3)^j, \qquad (1)$$

where U IS a selected strain energy function, and $I_1$ and $I_2$ are strain invariants, N=2 is most commonly used in modeling, $C_{ij}$ represents the hyper-elastic parameters, which determine the intrinsic nonlinear elastic properties of the tissues. The hyper-elastic parameters. $C_{ij}$, were optimized to best match the typical relation of the developed strain to applied strain from in vivo rat experiments. In the FE simulation, three inclusions with different stiffness were considered: soft inclusion mimicking the normal colon tissues, medium inclusion mimicking the acutely inflamed tissues, and hard inclusion mimicking the chronically fibrosed tissues.

A 1D linear array centered at 3 MHz with a fractional-bandwidth of 60% was used to generate 2D US RF data. To construct the US images, a 2D point spread function (PSF) was evaluated which closely mimics a typical commercially available liner ultrasound transducer. The axial PSF was determined assuming 60% fractional bandwidth and a Gaussian-type pulse envelope. The lateral and component was created such that the minimum in-plane f/number was 2. Each frame of digital RF data was then produced with 40 MHz sampling frequency by convolving the 2D PSF with the US scattering function. The scattering function was defined as the random distribution of scatterers over the entire tissue area. For each time-step of the FE simulation, the displacements of each of the scatterers were interpolated from the nodal solution and added to the pre-deformed coordinates to obtain the deformed scattering function. The speed of sound was assumed to be 1540 m/s in soft tissue. The scatterer density was set as 3 scatterers per wavelength. Each RF image with size of 60 mm×40 mm (corresponding to 3636 axial samples×256 beams) was generated at each time-step.

An Empirically Derived Nonlinear Equation

From both experimental data and FE-based simulation data, the developed strain-to-applied strain relation exhibits highly non-linear characteristics over the wide range of strains. To differentiate the target tissues with different stiffnesses, empirical curve fitting was performed by employing the Hill's equation, which was originally proposed for a muscle contraction study.

The adopted Hill equation to describe the strain-to-strain relation is as follows:

$$\varepsilon_d = \frac{A\varepsilon_a^n}{k^n + \varepsilon_a^n}, \qquad (2)$$

where: $\varepsilon_a$ is the applied strain, and $\varepsilon_d$ is the developed strain, and n is the model order, where k and A are arbitrary constants.

In our application, the order n determines the unique feature of the developed strain-to-applied strain curve of each inclusion and separates the inclusions with different stiffness from each other. The arbitrary k and A, which govern the onset shift of the curve and the amplitude of the tail of the curve, respectively, were adjusted to best fit each curve. The order n was then extracted further optimizing the fit to the curve. This procedure was identical for both simulation results and in vivo measurements. A commercial nonlinear least-squares optimization of the Levenberg-Marquardt algorithm in MATLAB from MathWorks was used for this purpose.

Results

Example 3

Nonlinear FE Simulation

A 2-D plane strain problem was formulated as shown in FIG. 8 for the numerical phantoms of the representative cases of soft, medium and hard inclusions.

Figure 9:
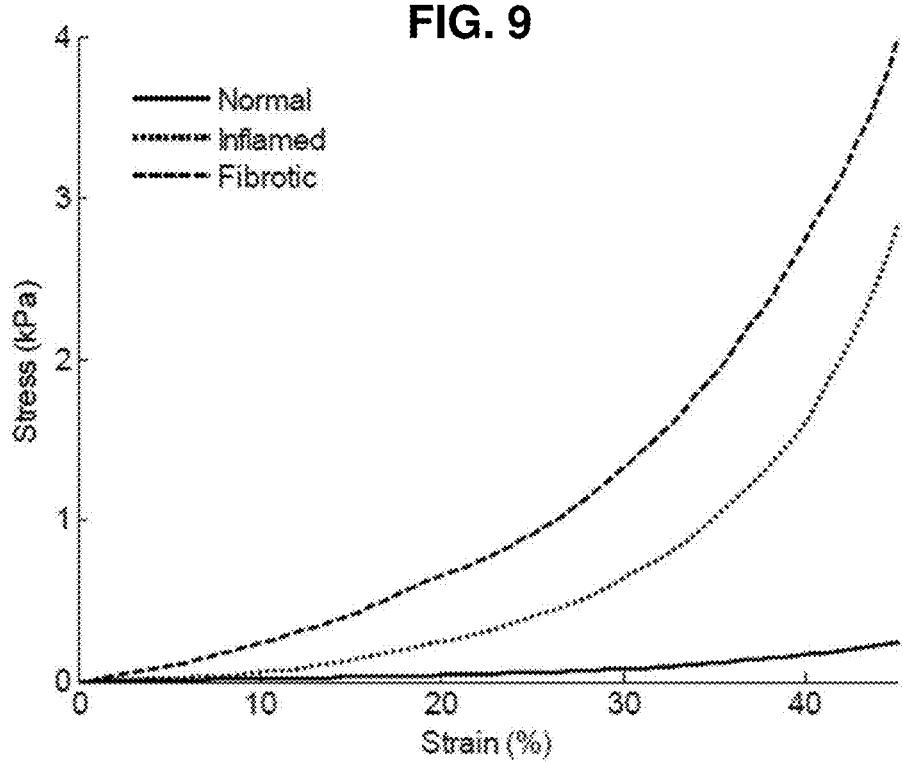
FIG. 9 illustrates stress-strain curves measured by the Microelastomer for the excised for normal (solid), acute (dotted), and chronic (dashed) tissues from the rats.

FIG. 9 illustrates the typical stress-strain curves measured by the Microelastomer for the excised for normal (solid), acute (dotted), and chronic (dashed) tissues from the rats. For FE simulation, these strain-stress curves in FIG. 9 were used as input to the inclusion model. In order to obtain similar elasticity contrast in the FE simulation to that of the in vivo animal experiments, the hyper-elastic parameters of the surrounding material, Cij, were adjusted until the developed strains inside the inclusion and the surrounding material become similar to the strains from the in vivo measurements. The average strain developed in the region of interest for the chronic group was about of 18% (±5%) under the applied average strain of 10% estimated from the displacement of the pelvis. The hyper-elastic parameters, Cij, were adjusted until the targeted inclusion developed 15% strain when the applied strain reached 10%. The non-linear coefficients for the hyper-elastic function were then set to be: $C_{01}=C_{10}=0.3$, and $C_{11}=2.25$, $C_{20}=3.8$, and $C_{02}=4.7$ for the fibrotic tissues. The hyper-elastic parameters for the other tissue types were almost identical. Therefore, the hyper-elastic parameters, $C_{ij}$, for the fibrotic tissues were used for all other cases in this study. This made the simulations consistent with the same background materials for inclusions with different stiffnesses.

Figure 10:
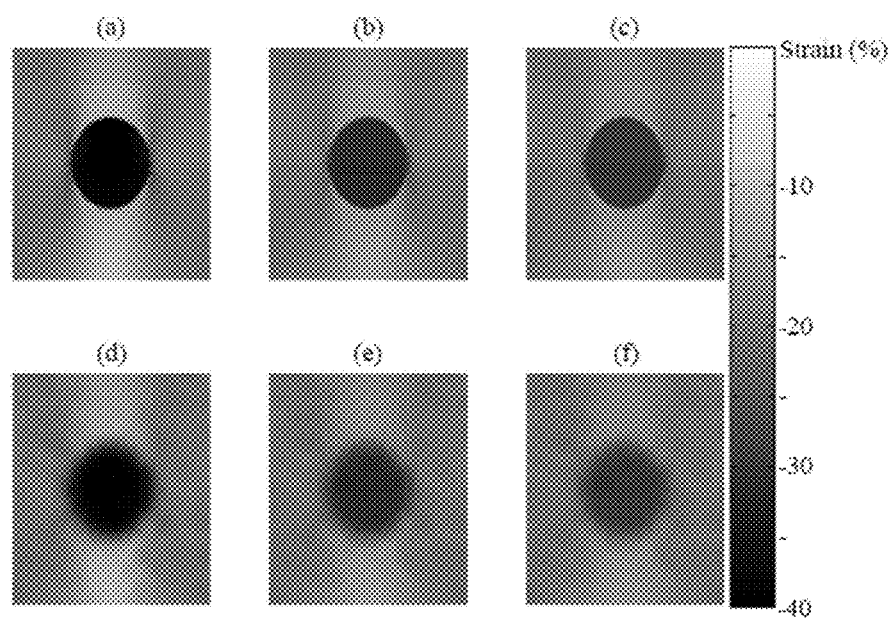
FIG. 10 illustrates accumulated strain estimates over the entire deformation from 2D speckle tracking.

Accumulated strain estimates over the entire deformation from 2D speckle tracking were compared with FE solutions in FIG. 10. The bottom row represents the strain maps from 2D speckle tracking for (d) a soft inclusion, (e) a medium inclusion, and (f) a hard inclusion, and the top row (a) (b) and (c) represents the strain map from FE solutions for the same inclusions, respectively. Overall, the strain maps from the speckle tracking compare well with the strain maps from the FE solutions. The average strain in every inclusion between the FE simulation and speckle tracking were also comparable. On the average, the relative error in average strain estimates between speckle tracking and FE simulation for every inclusion was less than 5%.

Figure 11:
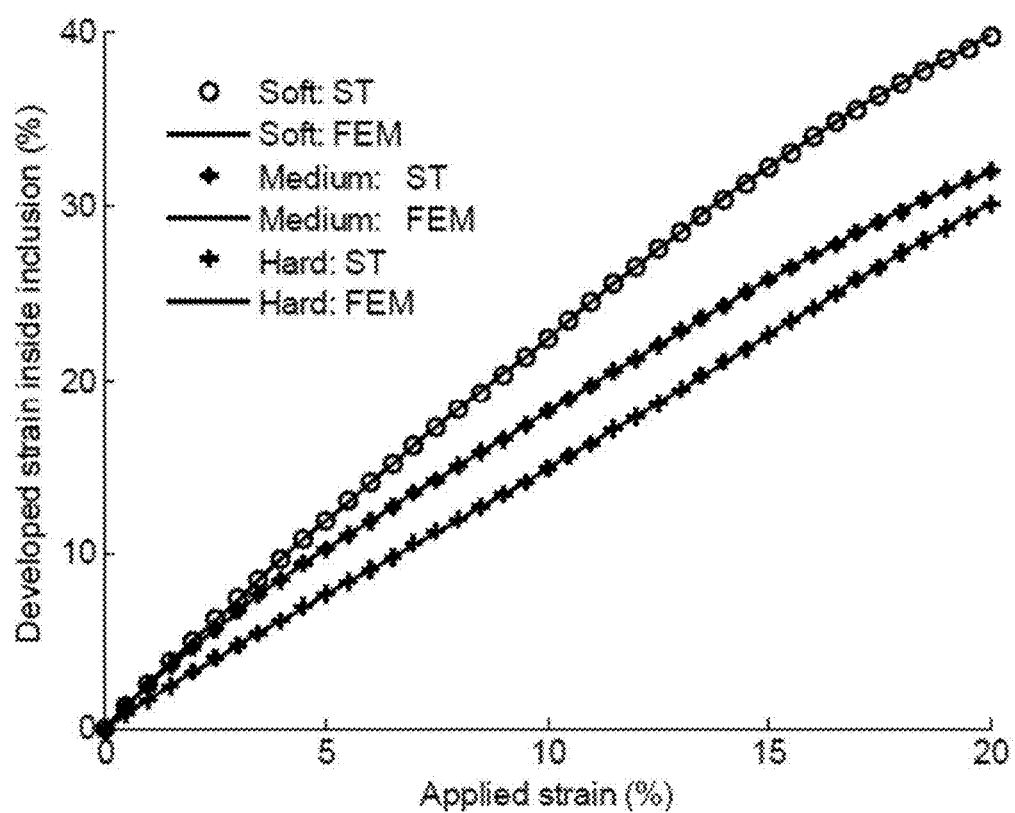
FIG. 11 illustrates the accumulated average strain for inclusions as plotted over the applied average strain.

In FIG. 11, the accumulated average strain in every inclusion is plotted over the applied average strain, which is exactly known in the FE simulation by pre-setting the total strain to 20% in 40 steps. In particular, the accumulated average strains from 2D speckle tracking for the soft inclusion (circles for Speckle tracking), medium inclusion (stars for speckle tracking), and hard inclusion (pluses for speckle tracking) are overlaid on their respective corresponding FE solutions in solid lines. The strain-to-strain curve for the hard inclusion is nearly linear in the applied strain range of 0% to 20%. The strain-to-strain curves for the soft and medium inclusions are both nonlinear in the applied strain range of 90% and 20%. The nonlinear FEM simulation result shows the different response curves for different stiffness, and demonstrates that the proposed nonlinear method is effective toward nonlinear elasticity imaging.

Accordingly, the hard inclusion generates overall less strain to the same amount of applied strain, and the soft and medium inclusions exhibit non-linear relations in strain-to-strain plots, while the hard inclusion maintains a generally straight line.

In Vivo Animal Experiments

Chronic/Fibrotic Group

Figure 12:
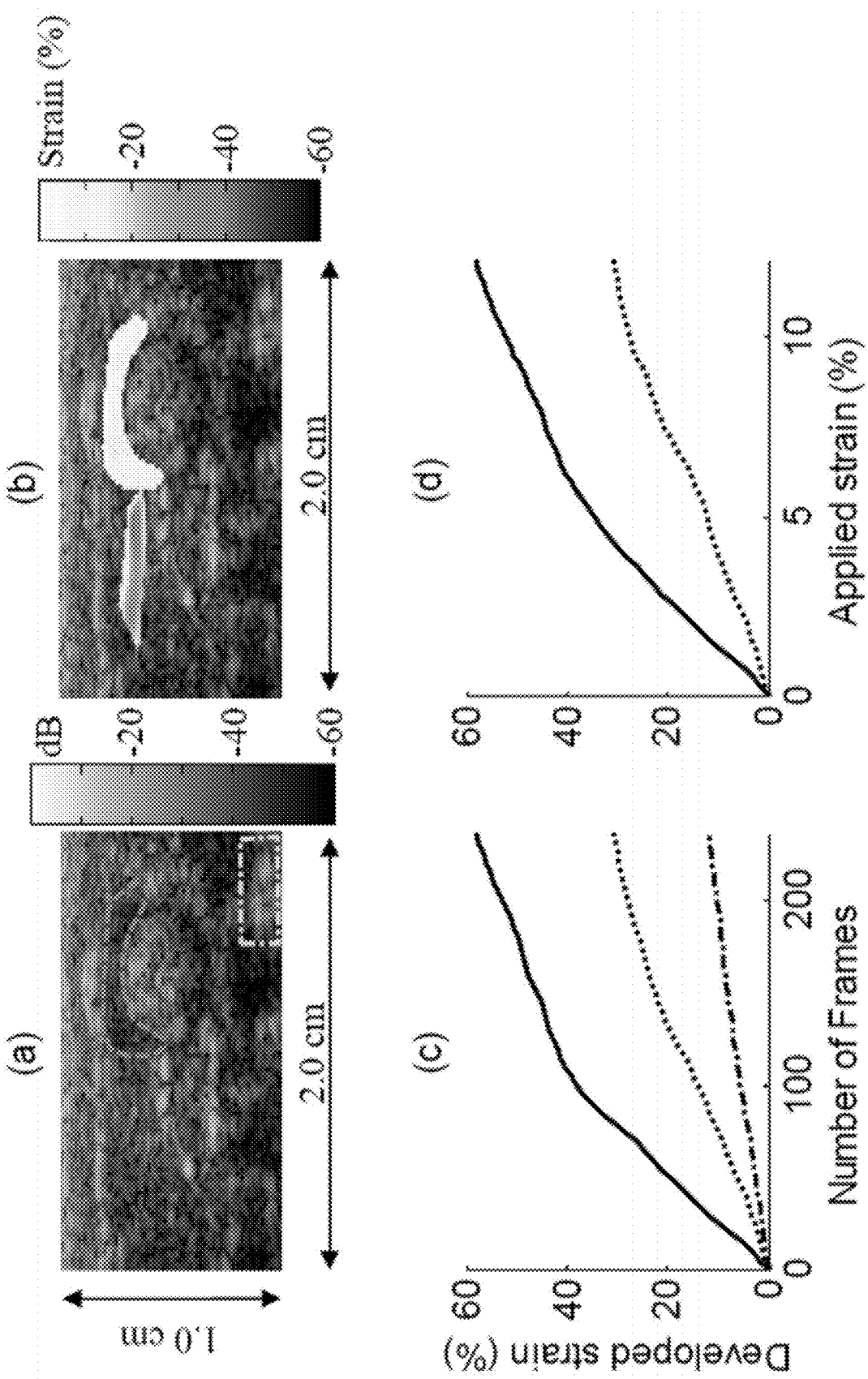
FIG. 12 illustrates the accumulated axial normal strain map over the 50 frames along with B-scan images for a representative chronically fibrotic case.

The accumulated axial normal strain map over the 50 frames along with B-scan images for a representative chronically fibrotic case are depicted in FIG. 12. In FIG. 12(a), the region enclosed by the dashed blue line indicates the ROI for the normal tissues, and the region enclosed by the dashed red line indicates the ROI for the fibrotic tissues. The dashed green box indicates the pelvis, which is used as the reference to obtain the average applied strain. In FIG. 12(b), the corresponding strain maps in the ROI are overlaid on the top of the B-scan images indicating the relative changes of the stiffness. The diseased fibrotic bowel developed less strain reflecting the increase in stiffness compared with the normal bowel of the rat.

FIG. 12(c) illustrates the accumulated average strain to the number of US frames inside normal (solid line) and fibrotic (dotted line) bowel. In (c), the dotted line is for the diseased bowel (chronically fibrosed) and the solid line is for the normal bowel, while the dash-dot is for the applied average strain estimated from the displacement of the pelvis and this line becomes the X-axis in (d). As shown in FIG. 12(c), the applied average strain was quite uniform, almost straight line (dash-dot), over the entire deformation procedure. The dashed-dot line presents the monotonically increasing applied average strain estimated from the displacement of the rat's pelvis. In FIG. 12(d), the same accumulated strains for normal and fibrotic bowel in FIG. 12(c) were plotted over the applied average strain. The overall characteristics of the fibrotic bowel in the developed strain-to-applied strain relation are differentiated from that of the normal bowel, which were observed in the FE simulation.

In Vivo Animal Experiments

Acute/Inflammatory Group

Figure 13:
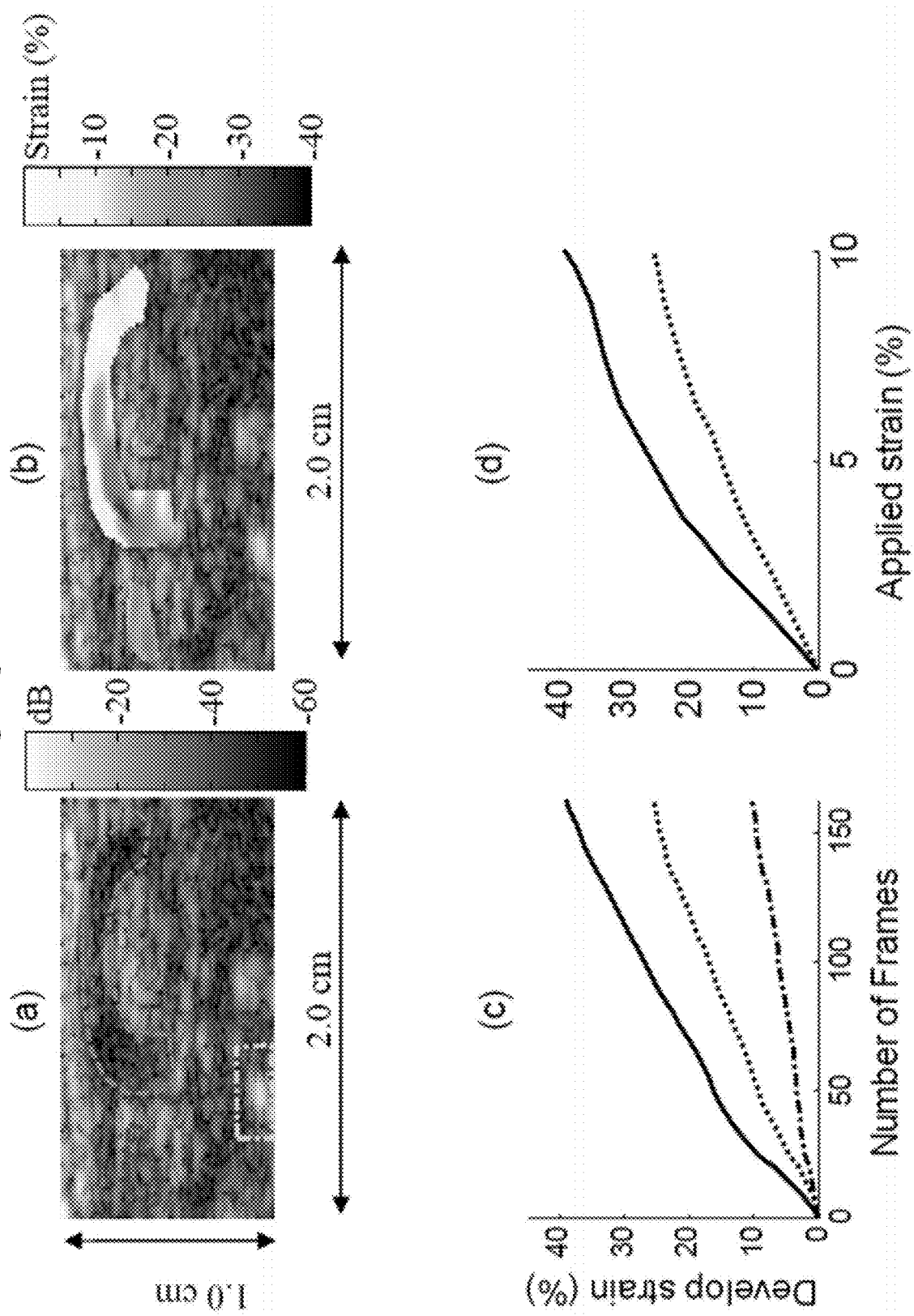
FIG. 13 illustrates the accumulated axial normal strain over the 50 frames along with B-scan images for a representative area of acutely inflamed bowel.

The accumulated axial normal strain over the 50 frames along with B-scan images for a representative area of acutely inflamed bowel is depicted in FIG. 13. B-mode images (a) and overlaid strain map (b), which is accumulated up to 156 frames with an applied average strain of about 10%. In FIG. 13(a), the region enclosed by the dashed blue line (upper left) indicates the ROI for the normal bowel, the region enclosed by the dashed red line (upper right) indicates the ROI for the acutely inflamed bowel. The dashed green box (lower center) indicates the pelvis, which is used as the reference to obtain the applied averaged strain. In FIG. 13(b), the corresponding strain maps in the ROIs are overlaid on the top of the B-scan images indicating the relative changes of the stiffness. The acutely inflamed bowel developed less strain reflecting the increase of the stiffness compared with the normal bowel.

FIG. 13(c) illustrates the accumulated strain to the number of US frames inside normal (solid line) and acutely inflamed (dotted line) bowel. The dashed-dot line presents monotonically increasing applied average strain estimated from the displacement of the rat's pelvis. In FIG. 13(d), the same accumulated strains for normal and acutely inflamed bowel in 6(c) were plotted over the applied averaged strain. The applied average strain was generally uniform, as reflected by the almost straight line (dash-dot), over the entire deformation procedure.

Non-Linear Curve Fitting for the Normal, Acute, and Chronic Tissues

In the rat study, the results from all 4 rats in the fibrotic group exhibit very similar developed strain-to-applied strain relations to the representative plot in FIG. 12 for the exemplary rat subject. The results for all 4 rats in the acute group also show very similar developed strain-to-applied strain relations to the representative plot in FIG. 13. All the normal bowel of 8 rat subjects in the untreated region also exhibit very similar strains.

In order to determine all possible solutions for the non-linear curve fitting, the initial values with (0,1) uniform random distributions for three parameters were run for 10,000 times, by looking at the distribution of model order n, there are four groups as: (1) n as complex (422/10,000), (2) n as negative 4306/10,000, (3) n is bigger than or equal to 4 or closer to zero (7/10,000), and (4) the rest estimates for n closer to 2 for the normal case (5265/10,000). All these solutions have mathematical meanings, but some of them do not have physical meanings like complex and negative orders. Throughout extensive random initial value testing, only the physically meaningful real and positive solutions of order n to Equation (2) are considered. Excluding all these non-real and non-physical estimated parameters from the nonlinear optimization, a unique positive solution for the order n was selected among all possible ones in the range of 0.5 to 4 for n, then we could select the positive unique optimal solution for non-linear problem.

Figure 14:
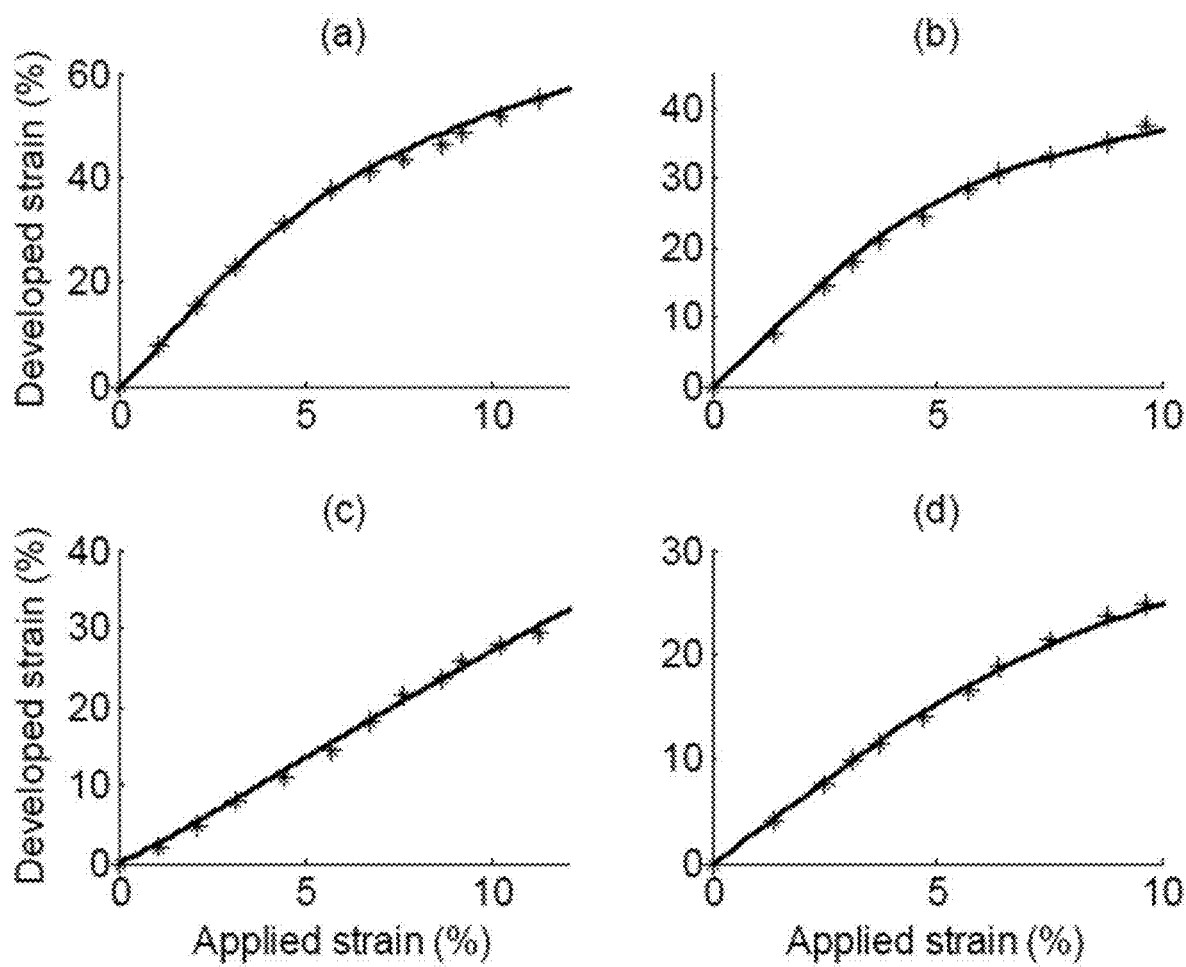
FIG. 14 illustrates the fitted curves of the equation (2) to the data for the fibrotic bowel (c), acutely inflamed bowel (d), and corresponding nearby normal bowel (a) and (b), respectively.

FIG. 14 presents the fitted curves of the equation (2) to the data for the fibrotic bowel (c), acutely inflamed bowel (d), and corresponding nearby normal bowel (a) and (b), respectively. The fitted curves are overlaid on top of experimental data. The non-linear parameter as the order n of equation (2) was determined to be 1.03 for the fibrotic (c), 1.50 for the inflamed (d), and 2.0 (a) and 1.9 (b) for the normal bowel of rats. Note the accumulated strain data points are arbitrarily parsed for presentation clarity.

The non-linear parameter n from the curve fittings to the equation (2) based on the FE simulation results also show distinct differences between the inclusions with different stiffness, where n is equal to 1.6 for the soft inclusion mimicking the normal bowel, 1.3 for the medium inclusion mimicking the acutely inflamed bowel, and 0.9 for the hard inclusion mimicking the chronically fibrotic bowel.

Figure 15:
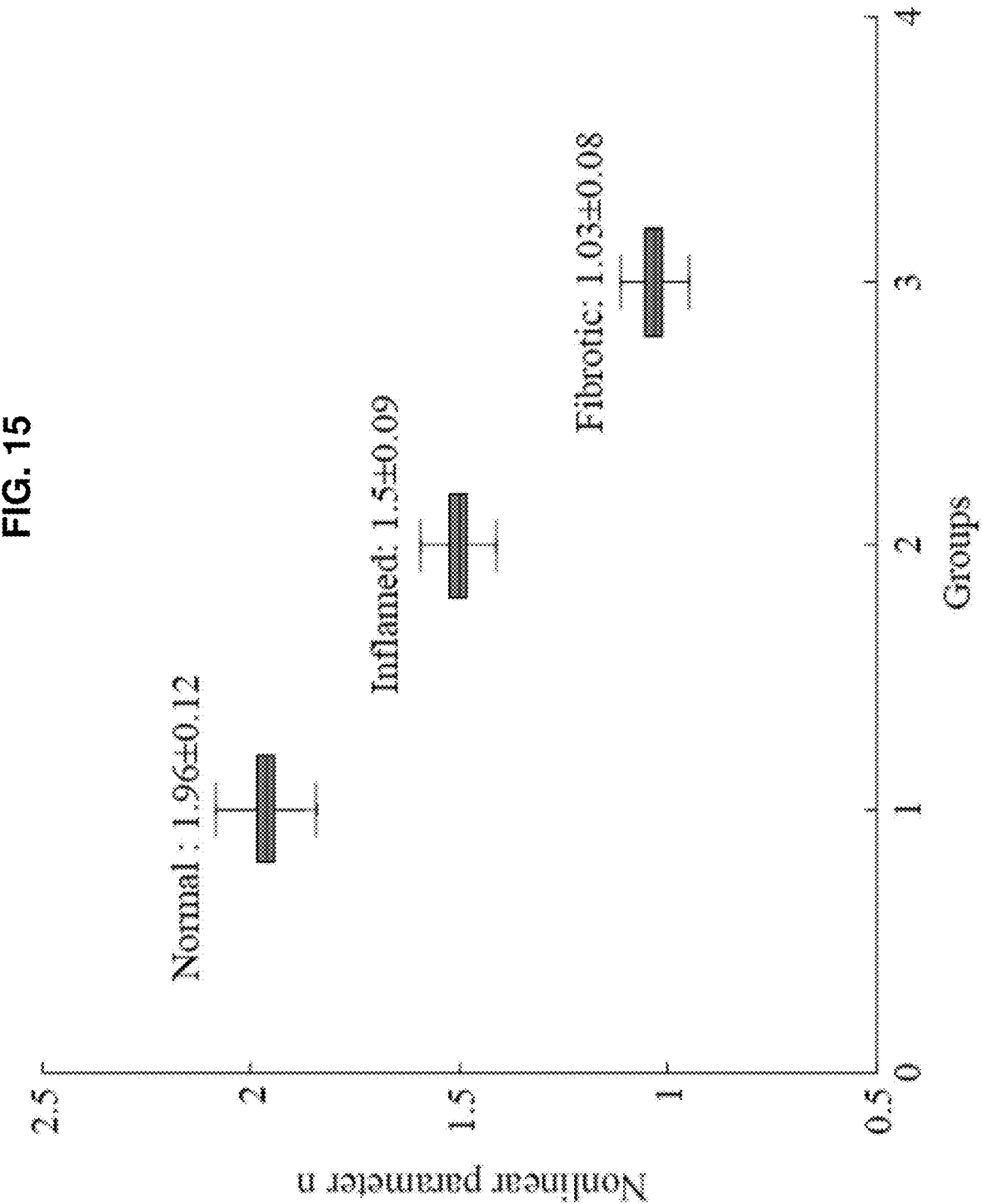
FIG. 15 illustrates nonlinear parameters for three groups of normal, acutely inflamed, and chronically-fibrosed bowels.

The average non-linear parameter n for each group was determined to be 1.96 with standard deviation of ±0.12 for the normal group, 1.5 with standard deviation of ±0.09 for the acute group, and for 1.03 with standard deviation of ±0.08 for the chronic group, as shown in FIG. 15. A t-tests determined that non-linear parameter between normal, acutely inflamed, and fibrotic groups were statistically significant (normal/fibrotic (P=0.0000185), normal/acutely inflamed (P=0.0013), and fibrotic/acutely inflamed (P=0.0029). The three different tissues were clearly separated by the non-linear parameter n with no overlap. In contrast, the conventional normalized average strain obtained at one state of the deformation does not fully differentiate the acutely inflamed bowel from the chronically fibrosed bowel with the normalized average strain (2.7 with standard deviation of ±0.4 for acute group, 2.6 with standard deviation of ±0.98 for chronic group, 5.6 with standard deviation of ±1.8 for the normal bowel). A t-tests determined that normalized strain between normal fibrotic groups and normal/acutely inflamed groups were statistically significant (normal/fibrotic (P=0.024), normal/acutely inflamed (P=0.022)), but not from each other for acutely inflamed/fibrotic (P=0.744).

Discussion Relating to Example 3

Accordingly, a novel nonlinear elastic parameter of the soft tissues was tested using a FE based nonlinear soft tissue model and in vivo animal model. To examine the nonlinear characteristics of the tissues over a relatively large dynamic range of strain, a simple nonlinear soft tissue model was established using FE methods where an inclusion of infinitely long cylinder was embedded in a homogenous surrounding tissue block. Within the range of the stiffness of the biological tissues of the animal model, including chronically developed fibrosis, acutely inflamed, and normal bowel tissues, the developed strain inside the inclusion vs. applied strain exhibit overall similar behaviors to those observed in the animal study.

As shown in FIG. 11, the developed strain-to-applied strain curve for soft, medium, and hard inclusions both from FE model and speckle tracking demonstrate similar trends with those of normal, acutely inflamed, and fibrotic bowel in the animal model, respectively, presented in FIGS. 12 and 13. The soft inclusion develops strain quite linearly at the beginning stage of the loading until the developed strain reaches the point where the material experiences nonlinear hardening effects, resulting in the saturation of the strain development. The hard inclusion develops overall less strain monotonically over the entire strain dynamic range of interest. The inclusion with medium stiffness exhibits almost the same strain as the soft inclusion, i.e. linearly at the onset of the loading up to a few percent of strain. Later, the strain, developed in the medium inclusion deviates from that of the soft inclusion, producing less strain and eventually exhibiting slight saturation of the strain, but distinct from the monotonic strain increase in the hard inclusion.

It is notable that the strain developed in the inclusion with medium stiffness is hardly differentiated from the strain developed in the soft inclusion at the beginning stage of the loading up to a few percent of strain, while at the later stage of the loading where the inclusion with medium stiffness experiences tissue hardening, it is more difficult to separate it from the hard inclusion. These trends were also observed in the direct mechanical measurements on the excised tissues as illustrated in the stress-strain curves in FIG. 9. The monotonic increase in the stress-strain relations for the normal (soft) and acutely inflamed (medium) bowel are very similar at the beginning stage of the loading, while the acutely inflamed bowel approach the fibrotic bowel in the stress-strain relation as they develop further strain and experience tissue hardening.

In animal model, in vivo strain estimates by speckle tracking also exhibit similar trends as illustrated in FIGS. 12 and 13. These characteristics can make it challenging to identify the acutely inflamed bowel using conventional UEI. At the onset of the deformation loading, acutely inflamed bowel develops strain much like the surrounding normal bowel. In addition, the relatively low signal-to-noise ratio of UEI at mild deformation loading in vivo makes UEI difficult to detect the acutely inflamed bowel. At higher deformation loading, the signal-to-noise ratio becomes high enough to estimate strain with less error, however, the stiffness of the acutely inflamed bowel tend to get closer to the chronically fibrosed bowel as they experience tissue hardening after the edematous water contents are forced out. This might be one of the fundamental limitations of the conventional UEI in identifying acutely inflamed tissues such as edema. It is believed that the accumulated water contents in the thickened edematous tissue due to inflammation would make the tissues softer until the liquid inside is squeezed out and the tissue becomes stiffer producing less strain to the applied deformation loading.

For convenience, the developed tissue model was simplified in two perspectives. The model includes a well-defined geometry of the inclusion and homogeneous surrounding tissue block, while the anatomy of the rat is more complicated. However, it is observed that the relatively soft abdomen of the rat absorbs the applied strain more or less uniformly enough to avoid any serious stress concentration around the bowel tissues of interest. The developed model also assumes a pure elastic model and does not include viscosity. Even if a visco-elastic model was performed, however, it would be challenging to assess the viscosity of the tissues using conventional UEI in vivo since liquid is relatively easily pushed away during the onset of deformation or mild pre loading, which often is required in UEI practice in vivo.

A simplified nonlinear hyper-elastic tissue model that exhibits the representative nonlinear characteristics of the tissues with different stiffness contrast to the background over large dynamic range of strain was provided. The accumulated strain at some point of the applied loading (strain), as shown in FIG. 11, can differentiate the inclusions with different stiffness. For example, the developed strains normalized to an applied strain of 10% in soft, medium and hard inclusions are 2.3, 1.8, and 1.5, respectively, thus differentiating the three groups. However, such a distinction becomes more difficult in vivo where strain estimates contain many more uncertainties, including (a) animal-to-animal variability, (b) ultrasound imaging and data acquisition system noise, and (c) out-of plane motion due to free hand deformation and non-uniform anatomical structure.

To quantitatively describe the nonlinear characteristics of the tissues with different stiffness contrast in the developed strain-to-applied strain relations, numerical curve fitting was performed. A very common equation for asymptotic relationships is known to be the Michealis-Menten equation or rectangular hyperbola, which is the special case of the Hill function with order 1. This equation has been employed in various different fields, including ecosystem modeling, biochemical characterization and molecular modeling. The unique asymptotic relationships among the variables were common characteristics in all these applications and were sufficient for this study. Curve fitting using Equation (2) was tested in simulation, supporting the fact that inclusions with different stiffness contrast can be differentiated with the variable n. Based on the empirically optimized variable n, normal, acutely inflamed, and chronically fibrotic bowel were successfully differentiated with variable n values of 1.96±0.12, 1.50±0.09, and 1.03±0.08, respectively with no overlap. A t-tests determined that non-linear parameter between normal, acutely inflamed, and fibrotic groups were statistically significant (normal/fibrotic (P=0.0000185), normal/acutely inflamed (P=0.0013), and acutely inflamed/fibrotic (P=0.0029). In contrast, the normalized strain using conventional UEI at average applied strain about 10% was estimated to be 5.6±1.8, 2.7±0.4, 2.6±0.98 for normal, acutely inflamed, and chronically fibrotic bowel, respectively, leaving the acutely inflamed bowel within the range of chronically fibrotic bowel. The stiffness of the acutely inflamed bowel was clearly separated from the chronically fibrotic bowel in the stress-strain relation from the direct mechanical measurements using the excised tissues. The fibrosis score from the histopathology, which are not presented in this paper, also supports the difference between two tissue statuses.

Estimating the applied strain can be challenging. For the animal study, the average strain was estimated with reasonable errors from the displacements of the pelvis or spine. However, it may be difficult to apply the same technique to the human subjects due to limited imaging depths. However, the use of lower frequency transducers will still permit strain estimates to be made at much greater imaging depths. Again, objects such as the pelvic wall, spine, and large posterior muscle groups such as iliopsoas should provide references for mean strain estimates very similar to those performed in rats. In addition, as described in more detail herein, a novel insert can be provided to improve the estimation of the applied strain and normalize any obtained measurements.

Accordingly, a new nonlinear parameter is provided to detect and characterize tissue mechanical property changes, especially subtle changes in stiffness such as those seen in acutely inflamed bowels. By determining a non-linear characteristic of the soft tissues over a relatively large dynamic range of strain, a sensitive and robust tool to assess subtle stiffness changes in tissues such as acutely inflamed bowel wall. This method can also be applied to other applications of ultrasound elasticity imaging with the proper adjustment of the involved nonlinear parameters in Equation (2) depending on the stiffness contrast of the tissues of interest.

Novel Inserts and Methods for Standardizing Results

Strains can be estimated by speckle tracking from ultrasound radio frequency signal during deformation. These strains are the relative distribution in the region of interest, and closely depend on the following parameters: (1) externally or internally applied loading or deformation; (2) the size of the external compressor; and (3) the surrounding tissues and structure and resulting boundary conditions. In order to compare the strains among different subjects or different scans on the same subject, normalization of the strains is required. In small animal studies, a nearby solid structure such as spine or pelvis can be used as relatively reasonable reference for the normalization; however this may vary depending on the different boundary conditions between subjects or scans on the same subject. Moreover, it is impractical to find a similar structure as reference due to the limited view and imaging depth in human subject studies.

Figure 16:
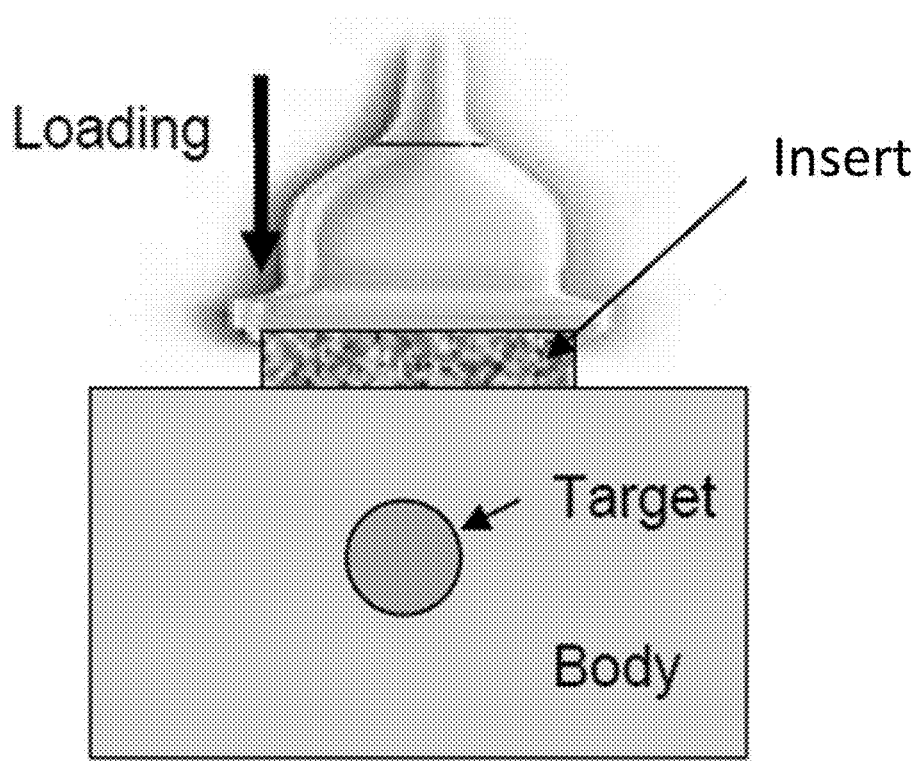
FIG. 16 illustrates an insert that provides a reliable and robust standardization method for measuring strain in soft tissue.

FIG. 16 illustrates an insert that provides a reliable and robust standardization method for measuring strain in soft tissue. The insert 100 can comprise an elastic insert with a known Young's modulus. In addition, the insert 100 can be generally ultrasonically transparent. The term "generally ultrasonically transparent" means that the insert is formed of a material that does not substantially interfere with the operation and measurements associated with an ultrasound device. For example, generally ultrasonically transparent inserts include inserts that are entirely transparent with no ultrasound scatters and those that are not entirely transparent with some ultrasound scatters. If an insert generates some ultrasound scatters when scanned by an ultrasound device, the insert is still generally ultrasonically transparent so long as the resulting attenuation is not significant enough to block the view of tissue through the insert. The relation of the applied strain—as measured from the insert—to the developed strain can be determined through an entire non-linear dynamic range of strain. In this manner, superior accuracy and sensitivity of strain measurements of tissue can be achieved.

A finite element (FE) based tissue and insert models were designed for simulation. The normalization scheme obtained from simulation was applied to in vitro phantom experiments using an elastic and ultrasonically transparent insert. The feasibility and practicality was shown by in vivo animal and human subject study.

As shown in FIG. 16, the insert can be placed between the top of surface of the area to be scanning (e.g., a surface of a patient) and the external surface of the ultrasound transducer. As shown in FIG. 16, the insert can be coupled to an external surface of the ultrasound transducer as an extended superficial structure in near field due to limited insert depth.

To provide the desired acoustical advantages, the insert can be made of a material that has low ultrasound attenuation and which does not significantly impact the imaging of the subject (e.g., the body). In this regard, the thickness of the insert should be selected to so that it is not too small, in which case it will not provide the desired image of the superficial structure and it will be difficult to measure the tiny deformation or very small displacement within the insert, or too deep, which will result in significant ultrasound attenuation due to a round trip within the insert and also potentially limit the frame rate due to increasing imaging depth by adding the insert. In one embodiment, the thickness is between about 5 and 30 mm, and, in some embodiments, between about 10 mm to 16 mm.

The elasticity properties of the insert can be selected to facilitate the normalization process and to withstand the repeated use of the insert, including the repeated load application to the insert. In addition, the insert should be a little harder than the normal soft tissue on which it will be used. If the insert is too soft, it will be easily reach to its maximum deformation until saturation and further deformation will not be measureable. On the other hand, if the insert is too stiff (hard), it will not undergo sufficient deformation to acquire the average strain from the insert. General acoustic measurement methods can be used to obtain the acoustic properties of the insert, the sound speed and ultrasound attenuation in the range from 0.5 MHz to 10 MHz.

The insert can be constructed of materials that are easy to clean, reusable, and cheap. In addition, the insert can be shaped to be easily attached to the ultrasound transducer and is desirably formed of a biocompatible material.

The insert can also be formed of a material that is sufficiently sturdy to not break or fail when pressure is applied to the insert and the tissue of the patient in the manner described herein. In some embodiments, the insert is sufficiently sturdy to experience an applied strain of at least 20%, and in some embodiments, at least 30%, without breaking or otherwise failing. In contrast, conventional ultrasound stand-offs cannot withstand such stains without breaking.

Figure 17A:
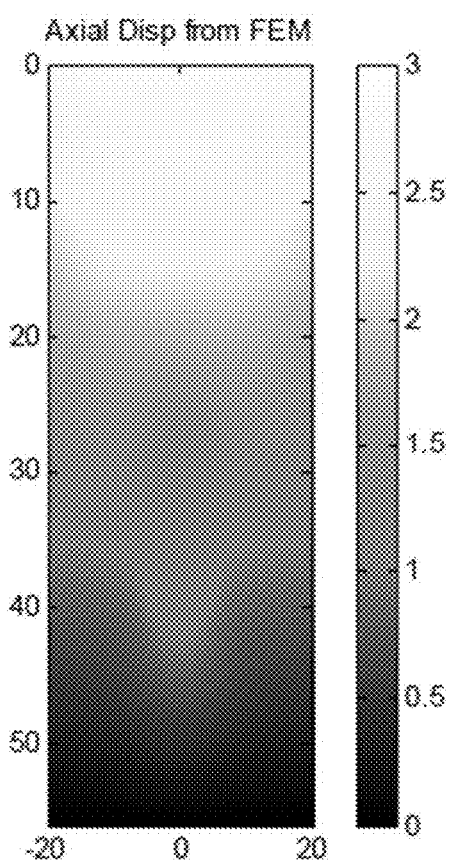
FIGS. 17A and 17B illustrate the comparison between the displacements estimated by finite element model (FIG. 17A) and ultrasound speckle tracking (FIG. 17B) for a numerical phantom with an inclusion.
Figure 17B:
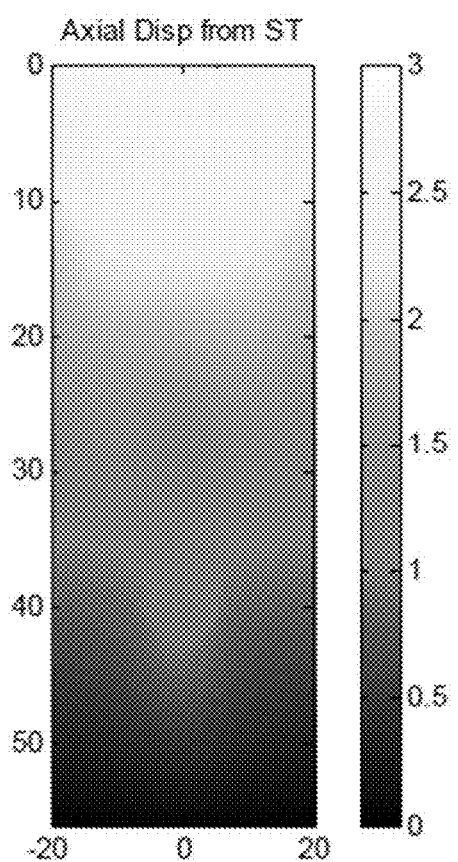

FIGS. 17A and 17B illustrate displacements as measured using FEM and speckle tracking (ST) at Young's Modulus ratio 0.1. In this example, the size of the ultrasound transducer is 40 mm, the Young's modulus for the insert (upper portion in figures) is 45 kPa, the Young's modulus for the body (lower portion in figures) is 30 kPa, and the Young's modulus for the inclusion (center of lower portion in figures) is 4.5 kPa.

Figure 18A:
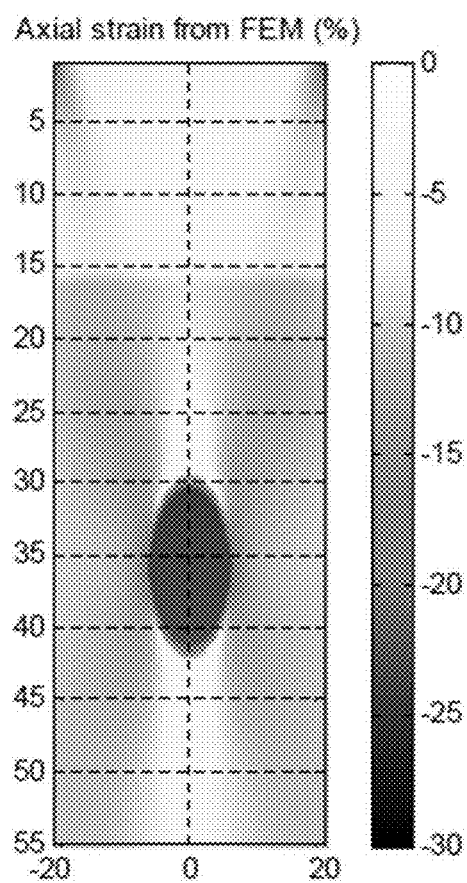
FIGS. 18A and 18B illustrate the comparison between the strains estimated by finite element model (FIG. 18A) and by ultrasound speckle tracking (FIG. 18B) for a numerical phantom with an inclusion.
Figure 18B:
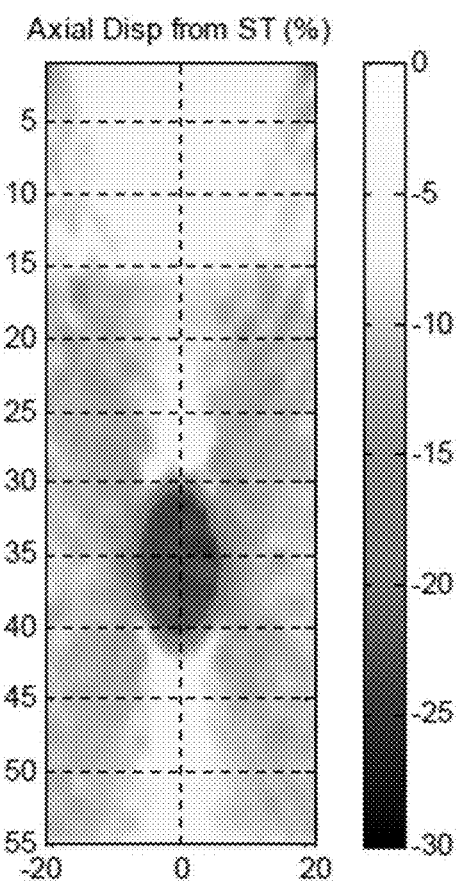

FIGS. 18A and 18B illustrate strain maps from FEM and speckle tracking with a Young's modulus ratio of 0.1.

Figure 19:
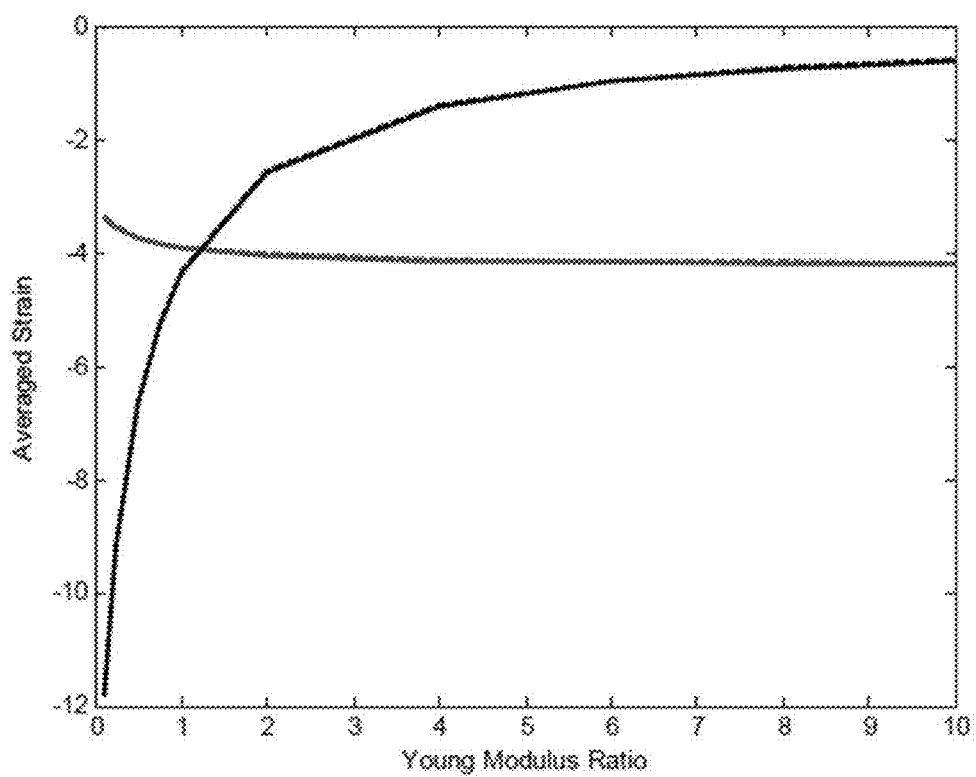
FIG. 19 illustrates the averaged strains developed in the insert estimated by finite element model (solid blue) and by ultrasound speckle tracing (dashed blue) and the averaged strains developed in the inclusion estimated by finite element model (solid back) and by ultrasound speckle tracking (dashed black).

FIG. 19 illustrates the averaged strains for the insert as determined using FEM (solid blue line) and ST (dashed blue line), and the averaged strains for the inclusion as determined using FEM (solid black line) and ST (dashed black line). As shown in FIG. 19, the FEM and ST curves are nearly identical for both the insert and inclusion. The maximum applied strain in this example is 5% and the response strain from the inclusion, body, or insert is less than 15%. Accordingly, linear FEM was used for this example.

Figure 20:
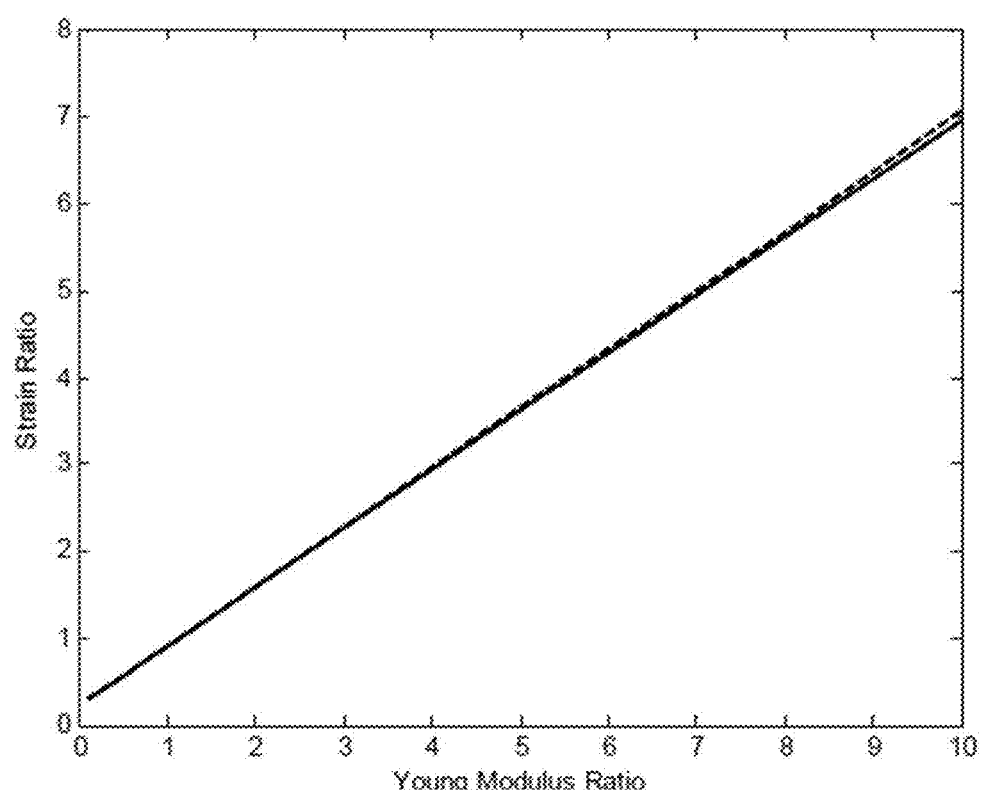
FIG. 20 illustrates the linear relation of the strain ratio (strain in the insert over the strain in the inclusion) to Young's modulus ratio (Young's modulus of the inclusion over the Young's modulus of the insert), with the solid line being representative of the finite element model and the dashed line being representative of ultrasound speckle tracking.

FIG. 20 illustrates a graph of strain ratio to Young's modulus ratio. The strain ratio is defined as the ratio of the insert's strain to an inclusion's strain, and Young's modulus ratio is defined as a ratio of the inclusion's Young's modulus to the insert's Young's modulus. The Young's modulus of the inclusion changes from 4.5 kPa to 450 kPa while the body and the insert are maintained with a fixed Young's modulus (45 kPa for the insert and 30 kPa for the body). The Young's modulus for the inclusion changes from 4.5 kPa to 450 kPa in the following order: 45*[0.1, 0.25, 0.5, 0.75, 1, 2, 4, 6, 8, 10]. Accordingly, the Young's modulus ratio is [0.1, 0.25, 0.5, 0.75, 1, 2, 4, 6, 8, 10]. The linear curve fitting for strain ratio to Young's modulus ratio from the FEM can be: y=0.675*x+0.223 (R=0.998), and the linear curve fitting for the strain ratio to Young's modulus ratio from the ST can be: y=0.686*x+0.22 (R=0.998).

Small differences between the FEM and ST curves may be noted since the strain map from speckle tracking cannot show the every small change and shape of the strain due to stress distribution, while the strain map from an FEM show such small changes and shapes of strain due to noise-less measurement of displacements.

Figure 21:
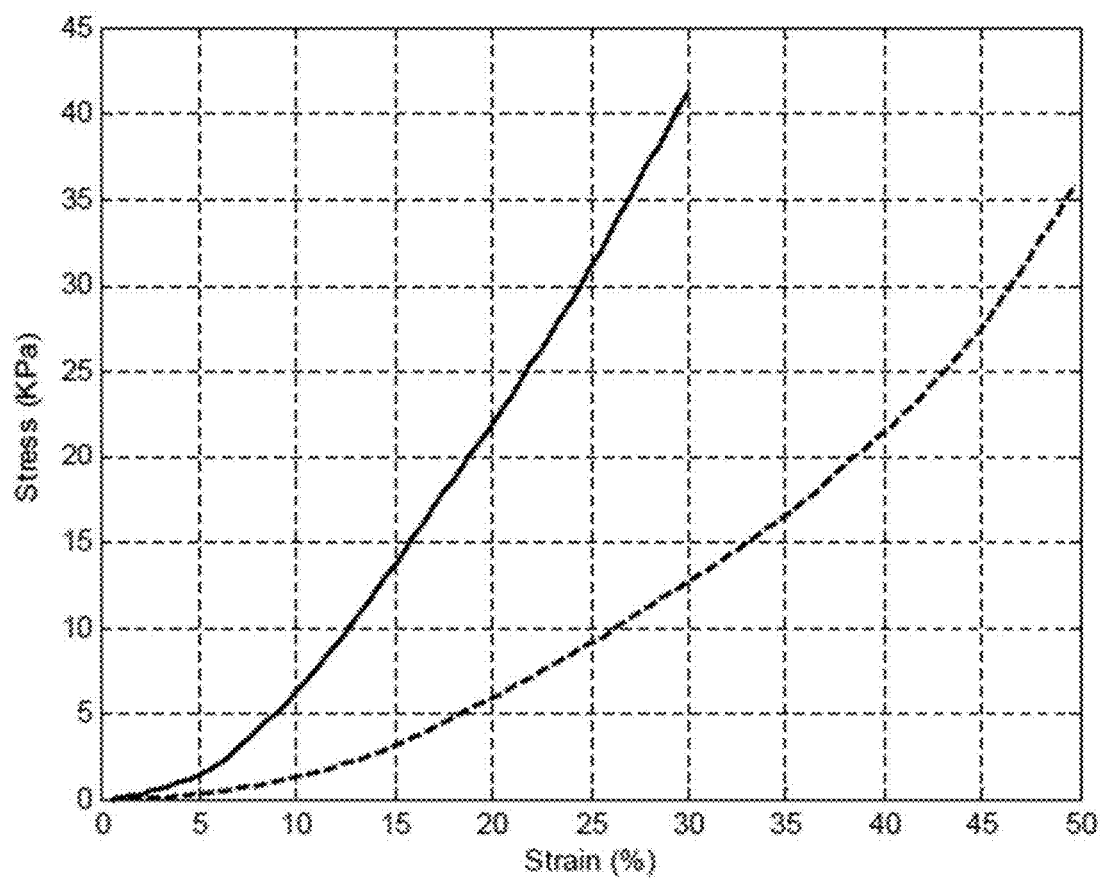
FIG. 21 illustrates the strain-stress curves of the insert of 30 kPa (dash curve) and the inclusion of 112.8 kPa (solid curve).

FIG. 21 illustrates exemplary strain-stress curves for an insert with a Young's modulus of 30 kPa (dashed line) and an inclusion with a Young's modulus of 112.8 kPa (solid line).

Figure 22:
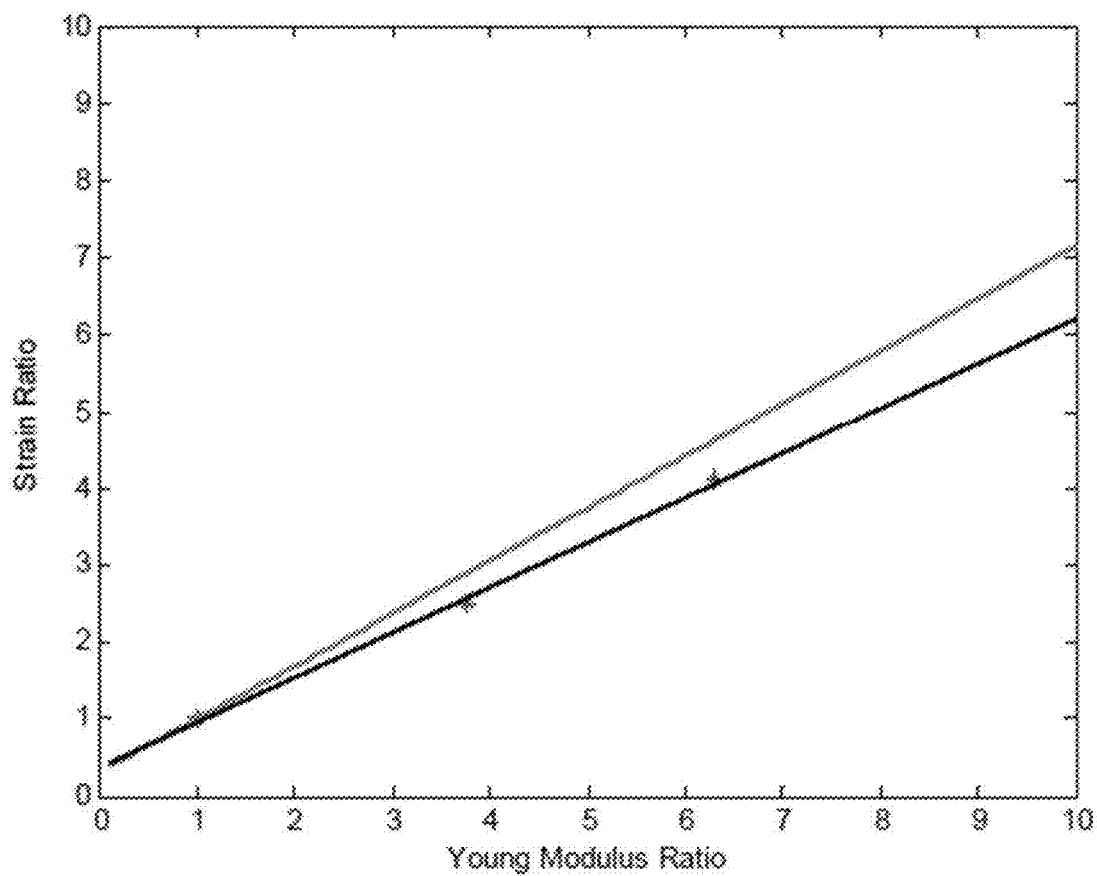
FIG. 22 illustrates the linear relation of the strain ratio (strain in the insert over the strain in the inclusion) to Young's modulus ratio (Young's modulus of the inclusion over the Young's modulus of the insert). The solid red line is from finite element model and asterisks are from tissue phantom experiments. The solid black is a linear fit to those three data points of tissue phantom experiments.
Figure 23:
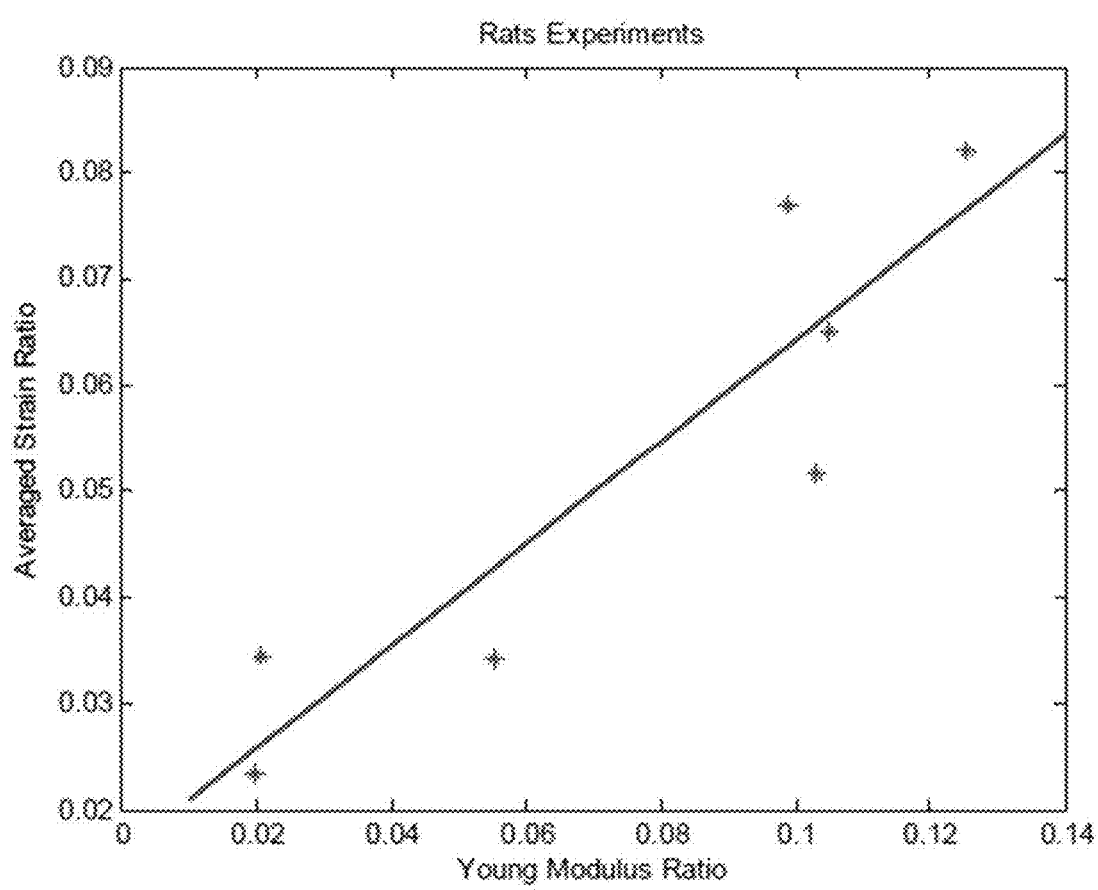
FIG. 23 illustrates the linear relation of the strain ratio (strain in the insert over the strain in the inclusion) to Young's modulus ratio (Young's modulus of the inclusion over the Young's modulus of the insert) of the excised tissues from rats.

FIG. 22 illustrates three plotted points (stars) from three examples. The three examples comprise phantoms of the same size but with different Young modulus for inclusions. The body material has a Young's modulus of 30 kPa, the insert has a Young's modulus of 30 kPa, and the Young's modulus for the first, second and third phantom's inclusions are 30 kPa, 112.8 kPa, 189 kPa, respectively. The slope for the strain ratio to Young's modulus (red curve) is 0.69 (Y=0.68495*ratio+0.31372;) from the FEM, and the black curve is the curve fitting for the phantom experiments, with the slope is being 0.58 (YL=0.58431*ratio+0.37918). FIG. 23 illustrates an exemplary strain ratio to Young's modulus ratio for rat subjects. In FIG. 23, the slope is 0.48 and the R value is 0.88.

In some embodiments, other elasticity parameters can be measured as a function of applied strain, either in addition to or as an alternative to developed strain. For example, in some embodiments, shear wave velocity can be measured as a function of applied strain in the same general manner as the measurement of developed strain described above. Shear wave velocity can be measured in various known manners, including, for example, performing spectral analysis and/or time domain analysis. Since displacement at different depths are under the same time frame, by performing spectral analysis of multiple displacements at various depths, phase information of each displacement can be used to extract a shear wave velocity. In time domain, the time delay estimate between the shear wave fronts at different time frames will determine a shear wave velocity. In operation, the methods described herein can be used except that sequential shear wave estimates are made (in addition to or in place of developed strain measurements) to measure and determine elasticity changes in the tissue as an applied strain is increased. When the modulus change is linear with applied strain, embodiments that measure shear wave velocity can substantially reduce and/or eliminate preloading effects.

Although the examples described herein are generally directed to determining and/or measuring tissue stiffness to identify conditions associated with Crohn's disease, it should be understood that the disclosed systems and methods can be used to determining and/or measuring tissue stiffness for other purposes as well, including, for example, in connection with diagnosing or treating any other condition or illness of which tissue stiffness is an indicator, factor, and/or result. For example, as noted above, in addition to Crohn's disease, UEI can be utilized in connection with many other diseases and/or conditions, including (1) thrombus aging/maturational evaluation in human lower limb deep venous thrombosis (DVT), (2) breast cancer diagnosis and screening, (3) differentiation of benign and malignant thyroid masses and cervical lymph nodes, (4) prostate cancer detection, (5) renal transplant graft nephropathy evaluation, (6) cardiovascular diseases, such as characterization of arterial wall stiffness for early atherosclerosis diagnosis, assessment of myocardial wall stiffness for detection of contractile dysfunction, or atheromata assessment for determining vulnerable plaque, and (7) liver diseases, such as assessment of the degree of liver fibrosis. The systems and methods described herein can be used in connection with these and other diseases and conditions where determining and measuring tissue stiffness can provide relevant information about a patient.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of using an insert to normalize measurements of tissue obtained by an ultrasound transducer, the method comprising:
    coupling an insert to an external surface of the ultrasound transducer;
    directing a plurality of ultrasound beams through the insert and into an area of tissue;
    acquiring a plurality of ultrasound echoes from the tissue and the insert to obtain tissue-based echo data and insert-based echo data;
    differentiating between the tissue-based echo data and the insert-based echo data; and
    normalizing a measurement of strain based on the tissue-based echo data obtained from the ultrasound echoes reflected by the insert from the plurality of ultrasound beams,
    wherein the insert-based echo data comprises speckle tracking data calculated from the ultrasound echoes reflected by the insert.

2. The method of claim 1, further comprising:
    applying a first amount of force to the area of tissue to provide a first amount of applied strain on the area of tissue; and
    calculating the first amount of applied strain on the area of tissue using speckle tracking.

3. The method of claim 2, further comprising:
    applying a second amount of force to the area of tissue to provide a second amount of applied strain on the area of tissue; and
    calculating the second amount of applied strain on the area of tissue using speckle tracking.

4. The method of claim 1, wherein force is continuously increased from the application of the first force to the application of the second force, and a varying amount of applied strain on the area of tissue is continuously calculated from the application of the first force to the application of the second force.

5. The method of claim 4, further comprising:
    extracting a nonlinear parameter from the relationship between a developed strain and the applied strain to identify a stiffness characteristic of the area of tissue.

6. The method of claim 1, wherein the Young's modulus of the insert is known.

7. The method of claim 1, wherein the insert has a thickness that is between 5 mm and 30 mm.

8. The method of claim 1, wherein the insert has a thickness that is between 10 mm and 16 mm.

* * * * *